(12) United States Patent
Roschak et al.

(10) Patent No.: US 7,422,563 B2
(45) Date of Patent: Sep. 9, 2008

(54) MULTIFUNCTIONAL TIP CATHETER FOR APPLYING ENERGY TO TISSUE AND DETECTING THE PRESENCE OF BLOOD FLOW

(75) Inventors: Ed Roschak, Mountain View, CA (US); Thomas Keast, Mountain View, CA (US); Hewlett E. Melton, Jr., Sunnyvale, CA (US); Christopher Lee Willink, Mountain View, CA (US); Dave Haugaard, San Jose, CA (US); David Thompson, San Jose, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 0 days.

(21) Appl. No.: 10/080,344

(22) Filed: Feb. 21, 2002

(65) Prior Publication Data

US 2002/0128647 A1    Sep. 12, 2002

Related U.S. Application Data

(63) Continuation-in-part of application No. 09/946,706, filed on Sep. 4, 2001, now Pat. No. 6,749,606, which is a continuation-in-part of application No. 09/908,087, filed on Jul. 18, 2001, now abandoned, which is a continuation of application No. 09/633,651, filed on Aug. 7, 2000, now Pat. No. 6,692,494.

(60) Provisional application No. 60/269,130, filed on Feb. 14, 2001, provisional application No. 60/176,141, filed on Jan. 14, 2000, provisional application No. 60/147,528, filed on Aug. 5, 1999.

(51) Int. Cl.
  *A61B 18/04*    (2006.01)
(52) U.S. Cl. ............................................. 601/2; 606/41

(58) Field of Classification Search ................ 600/437, 600/438, 439, 453, 427; 601/2, 3; 606/27, 606/28, 32–34, 41
See application file for complete search history.

(56) References Cited

U.S. PATENT DOCUMENTS 2,127,903 A    8/1938    Bowen (Continued)

FOREIGN PATENT DOCUMENTS

DE    3821836 A1    1/1990

(Continued)

OTHER PUBLICATIONS

Paterra™ (Version 1.5) Machine Translation of JP 2000-107178, pp. 1-31.

(Continued)

*Primary Examiner*—Roy D. Gibson
*Assistant Examiner*—Aaron Roane
(74) *Attorney, Agent, or Firm*—Levine Bagade Han LLP

(57) ABSTRACT

Disclosed herein are devices for altering gaseous flow within a lung to improve the expiration cycle of an individual, particularly individuals having Chronic Obstructive Pulmonary Disease (COPD). More particularly, devices are disclosed to produce collateral openings or channels through the airway wall so that expired air is able to pass directly out of the lung tissue to facilitate both the exchange of oxygen ultimately into the blood and/or to decompress hyper-inflated lungs.

16 Claims, 12 Drawing Sheets

U.S. PATENT DOCUMENTS

| | | |
|---|---|---|
| 3,174,851 A | 3/1965 | Buehler et al. |
| 3,351,463 A | 11/1967 | Rozner et al. |
| 3,433,226 A | 3/1969 | Boyd |
| 3,556,079 A | 1/1971 | Omizo |
| 3,565,062 A | 2/1971 | Kuris |
| 3,617,060 A | 11/1971 | Leggi |
| 3,753,700 A | 8/1973 | Harrison et al. |
| 3,779,234 A | 12/1973 | Eggleton et al. |
| 3,823,717 A | 7/1974 | Pohlman et al. |
| 3,942,530 A | 3/1976 | Northeved |
| 4,249,539 A | 2/1981 | Vilkomerson et al. |
| 4,249,541 A | 2/1981 | Pratt |
| 4,319,580 A * | 3/1982 | Colley et al. ............... 600/453 |
| 4,355,426 A | 10/1982 | MacGregor |
| 4,407,294 A | 10/1983 | Vilkomerson |
| 4,431,006 A | 2/1984 | Trimmer et al. |
| 4,503,569 A | 3/1985 | Dotter |
| 4,534,761 A | 8/1985 | Raible |
| 4,538,618 A | 9/1985 | Rosenberg et al. |
| 4,582,067 A | 4/1986 | Silverstein et al. |
| 4,583,969 A | 4/1986 | Mortensen |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,769,031 A | 9/1988 | McGough |
| 4,770,185 A | 9/1988 | Silverstein et al. |
| 4,771,788 A | 9/1988 | Millar |
| 4,773,413 A | 9/1988 | Hussein et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,869,268 A | 9/1989 | Yoon |
| 4,870,953 A | 10/1989 | DonMicheal et al. |
| 4,887,606 A * | 12/1989 | Yock et al. ............... 600/461 |
| 4,892,098 A | 1/1990 | Sauer |
| 4,899,757 A | 2/1990 | Pope, Jr. et al. |
| 4,917,097 A | 4/1990 | Proudian, et al. |
| 4,920,954 A | 5/1990 | Alliger et al. |
| 4,924,863 A | 5/1990 | Sterzer |
| 4,936,281 A | 6/1990 | Stasz |
| 4,957,508 A | 9/1990 | Kaneko et al. |
| 4,967,753 A | 11/1990 | Haase et al. |
| 4,973,301 A | 11/1990 | Nissenkorn |
| 4,977,898 A | 12/1990 | Schwarzschild et al. |
| 5,002,058 A | 3/1991 | Martinelli |
| 5,030,201 A | 7/1991 | Palestrant |
| 5,042,981 A * | 8/1991 | Gross ............... 606/32 |
| 5,054,483 A | 10/1991 | Marten et al. |
| 5,061,275 A | 10/1991 | Wallstén et al. |
| 5,064,435 A | 11/1991 | Porter |
| 5,069,664 A | 12/1991 | Suess et al. |
| 5,081,993 A | 1/1992 | Kitney et al. |
| 5,100,423 A | 3/1992 | Fearnot |
| 5,105,816 A | 4/1992 | Shimura et al. |
| 5,105,817 A | 4/1992 | Uchibori et al. |
| 5,125,926 A | 6/1992 | Linhares et al. |
| 5,127,917 A | 7/1992 | Niederhauser et al. |
| 5,131,394 A | 7/1992 | Gehlbach |
| 5,148,809 A | 9/1992 | Biegeleisen-Knight et al. |
| 5,170,793 A | 12/1992 | Takano et al. |
| 5,190,528 A | 3/1993 | Fonger et al. |
| 5,201,316 A | 4/1993 | Pomeranz et al. |
| 5,209,721 A | 5/1993 | Wilk |
| 5,226,421 A | 7/1993 | Frisbie et al. |
| 5,238,027 A | 8/1993 | Lee |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,269,326 A | 12/1993 | Verrier |
| 5,273,529 A | 12/1993 | Idowu |
| 5,275,166 A | 1/1994 | Vaitekunas et al. |
| 5,282,824 A | 2/1994 | Gianturco |
| 5,287,861 A | 2/1994 | Wilk |
| 5,295,484 A * | 3/1994 | Marcus et al. ............... 600/439 |
| 5,299,578 A | 4/1994 | Rotteveel et al. |
| 5,309,915 A | 5/1994 | Ember |
| 5,311,871 A | 5/1994 | Yock |
| 5,313,950 A | 5/1994 | Ishikawa et al. |
| 5,316,001 A * | 5/1994 | Ferek-Petric et al. ........ 600/454 |
| 5,320,106 A | 6/1994 | Tanaka |
| 5,330,500 A | 7/1994 | Song |
| 5,334,183 A | 8/1994 | Wuchinich |
| 5,334,210 A | 8/1994 | Gianturco |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A * | 1/1995 | Ueno et al. ............... 600/446 |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,470,308 A | 11/1995 | Edwards et al. |
| 5,474,075 A | 12/1995 | Goldberg et al. |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,514,154 A | 5/1996 | Lau et al. |
| 5,520,684 A | 5/1996 | Imran |
| 5,522,822 A | 6/1996 | Phelps et al. |
| 5,527,292 A | 6/1996 | Adams et al. |
| 5,527,324 A | 6/1996 | Krantz et al. |
| 5,540,713 A | 7/1996 | Schnepp-Pesch et al. |
| 5,545,195 A | 8/1996 | Lennox et al. |
| 5,545,210 A | 8/1996 | Hess et al. |
| 5,554,118 A | 9/1996 | Jang |
| 5,554,152 A | 9/1996 | Aita et al. |
| 5,555,886 A | 9/1996 | Weng et al. |
| 5,564,434 A | 10/1996 | Halperin et al. |
| 5,571,086 A | 11/1996 | Kaplan et al. |

| | | | | | | |
|---|---|---|---|---|---|---|
| 5,571,180 A | 11/1996 | Blom | | 5,993,484 A | 11/1999 | Shmulewitz |
| 5,573,531 A | 11/1996 | Gregory | | 6,001,124 A | 12/1999 | Bachinski |
| 5,575,818 A | 11/1996 | Pinchuk | | 6,002,955 A | 12/1999 | Willems et al. |
| 5,588,432 A | 12/1996 | Crowley | | 6,003,517 A | 12/1999 | Sheffield et al. |
| 5,593,417 A | 1/1997 | Rhodes | | 6,004,269 A | 12/1999 | Crowley et al. |
| 5,596,989 A | 1/1997 | Morita | | 6,004,273 A | 12/1999 | Sakamoto et al. |
| 5,607,444 A | 3/1997 | Lam | | 6,004,319 A | 12/1999 | Gobel et al. |
| 5,615,679 A | 4/1997 | Ri et al. | | 6,007,544 A | 12/1999 | Kim |
| 5,618,301 A | 4/1997 | Hauenstein et al. | | 6,007,574 A | 12/1999 | Pulnev et al. |
| 5,630,837 A | 5/1997 | Crowley | | 6,010,529 A | 1/2000 | Herweck et al. |
| D380,266 S | 6/1997 | Boatman et al. | | 6,011,995 A | 1/2000 | Guglielmi et al. |
| 5,645,559 A | 7/1997 | Hachtman et al. | | 6,013,033 A | 1/2000 | Berger et al. |
| 5,647,871 A | 7/1997 | Levine et al. | | 6,013,093 A | 1/2000 | Nott et al. |
| 5,653,746 A | 8/1997 | Schmitt | | 6,013,854 A | 1/2000 | Moriuchi |
| 5,655,548 A | 8/1997 | Nelson et al. | | 6,015,405 A | 1/2000 | Schwartz et al. |
| 5,658,279 A | 8/1997 | Nardella et al. | | 6,019,787 A | 2/2000 | Richard et al. |
| 5,658,280 A | 8/1997 | Issa | | 6,022,371 A | 2/2000 | Killion et al. |
| 5,672,172 A | 9/1997 | Zupkas | | 6,024,703 A | 2/2000 | Zanelli et al. |
| 5,674,277 A | 10/1997 | Freitag | | 6,030,392 A | 2/2000 | Dakov |
| 5,674,298 A | 10/1997 | Levy et al. | | 6,032,674 A | 3/2000 | Eggers et al. |
| 5,678,555 A | 10/1997 | O'Connell | | 6,036,702 A | 3/2000 | Bachinski et al. |
| 5,693,085 A | 12/1997 | Buirge et al. | | 6,045,511 A | 4/2000 | Ott et al. |
| 5,704,361 A | 1/1998 | Seward et al. | | 6,045,532 A | 4/2000 | Eggers et al. |
| 5,713,949 A | 2/1998 | Jayaraman | | 6,048,362 A | 4/2000 | Berg |
| 5,716,393 A | 2/1998 | Lindenberg et al. | | 6,053,941 A | 4/2000 | Lindenberg et al. |
| 5,718,701 A * | 2/1998 | Shai et al. ............. 606/41 | | 6,059,731 A | 5/2000 | Seward et al. |
| 5,720,735 A | 2/1998 | Dorros | | 6,059,811 A | 5/2000 | Pinchasik et al. |
| 5,725,547 A | 3/1998 | Chuter | | 6,063,111 A | 5/2000 | Hieshima et al. |
| 5,736,642 A | 4/1998 | Yost et al. | | 6,064,902 A | 5/2000 | Haissaguerre et al. |
| 5,741,234 A | 4/1998 | Aboul-Hosn | | 6,068,638 A | 5/2000 | Makower |
| 5,741,333 A | 4/1998 | Frid | | 6,070,094 A | 5/2000 | Swanson et al. |
| 5,752,518 A | 5/1998 | McGee et al. | | 6,074,349 A | 6/2000 | Crowley |
| 5,755,769 A | 5/1998 | Richard et al. | | 6,074,416 A | 6/2000 | Berg et al. |
| 5,755,778 A | 5/1998 | Kleshinski | | 6,080,109 A | 6/2000 | Baker et al. |
| 5,759,769 A | 6/1998 | Sia et al. | | 6,096,053 A | 8/2000 | Bates |
| 5,779,642 A | 7/1998 | Nightengale | | 6,112,123 A | 8/2000 | Kelleher et al. |
| 5,792,119 A | 8/1998 | Marx | | 6,113,612 A | 9/2000 | Swanson et al. |
| 5,795,325 A | 8/1998 | Valley et al. | | 6,117,101 A | 9/2000 | Diederich et al. |
| 5,797,920 A | 8/1998 | Kim | | 6,120,432 A | 9/2000 | Sullivan et al. |
| 5,810,008 A | 9/1998 | Dekel et al. | | 6,129,726 A | 10/2000 | Edwards et al. |
| 5,810,836 A | 9/1998 | Hussein et al. | | 6,135,997 A * | 10/2000 | Laufer et al. ............. 606/27 |
| 5,824,046 A | 10/1998 | Smith et al. | | 6,143,019 A | 11/2000 | Motamedi et al. |
| 5,830,191 A | 11/1998 | Hildwein et al. | | 6,152,937 A | 11/2000 | Peterson et al. |
| 5,830,222 A | 11/1998 | Makower | | 6,152,945 A | 11/2000 | Bachinski et al. |
| 5,840,431 A | 11/1998 | Kall | | 6,159,225 A | 12/2000 | Makower |
| 5,843,175 A | 12/1998 | Frantzen | | 6,162,245 A | 12/2000 | Jayaraman |
| 5,846,205 A | 12/1998 | Curley et al. | | 6,165,127 A | 12/2000 | Crowley |
| 5,849,037 A | 12/1998 | Frid | | 6,174,323 B1 | 1/2001 | Biggs et al. |
| 5,855,597 A | 1/1999 | Jayaraman | | 6,183,444 B1 | 2/2001 | Glines et al. |
| 5,860,920 A | 1/1999 | McGee et al. | | 6,186,942 B1 | 2/2001 | Sullivan et al. |
| 5,860,951 A | 1/1999 | Eggers et al. | | 6,190,353 B1 | 2/2001 | Makower et al. |
| 5,868,763 A | 2/1999 | Spence et al. | | 6,200,313 B1 | 3/2001 | Abe et al. |
| 5,876,345 A | 3/1999 | Eaton et al. | | 6,206,831 B1 * | 3/2001 | Suorsa et al. ............. 600/439 |
| 5,876,434 A | 3/1999 | Flomenblit et al. | | 6,231,587 B1 | 5/2001 | Makower |
| 5,876,448 A | 3/1999 | Thompson et al. | | 6,235,024 B1 * | 5/2001 | Tu ............. 606/41 |
| 5,885,219 A | 3/1999 | Nightengale | | 6,235,054 B1 | 5/2001 | Berg et al. |
| 5,916,158 A * | 6/1999 | Webster, Jr. ............. 600/374 | | 6,241,742 B1 | 6/2001 | Spence et al. |
| 5,921,995 A | 7/1999 | Kleshinski | | 6,241,746 B1 | 6/2001 | Bosma et al. |
| 5,922,019 A | 7/1999 | Hankh et al. | | 6,245,020 B1 | 6/2001 | Moore et al. |
| 5,935,135 A | 8/1999 | Bramfitt et al. | | 6,245,102 B1 | 6/2001 | Jayaraman |
| 5,938,697 A | 8/1999 | Killion et al. | | 6,258,100 B1 | 7/2001 | Alferness et al. |
| 5,951,567 A | 9/1999 | Javier, Jr. et al. | | 6,258,115 B1 | 7/2001 | Dubrul |
| 5,954,649 A | 9/1999 | Chia et al. | | 6,270,524 B1 | 8/2001 | Kim |
| 5,957,849 A | 9/1999 | Munro | | 6,280,457 B1 | 8/2001 | Wallace et al. |
| 5,957,919 A | 9/1999 | Laufer | | 6,283,951 B1 | 9/2001 | Flaherty et al. |
| 5,957,974 A | 9/1999 | Thompson et al. | | 6,283,983 B1 | 9/2001 | Makower et al. |
| 5,967,990 A | 10/1999 | Thierman et al. | | 6,287,290 B1 | 9/2001 | Perkins et al. |
| 5,968,053 A | 10/1999 | Revelas | | 6,290,728 B1 | 9/2001 | Phelps et al. |
| 5,968,070 A | 10/1999 | Bley et al. | | 6,293,951 B1 | 9/2001 | Alferness et al. |
| 5,971,980 A | 10/1999 | Sherman | | 6,299,635 B1 | 10/2001 | Frantzen |
| 5,972,017 A | 10/1999 | Berg et al. | | 6,309,375 B1 | 10/2001 | Glines et al. |
| 5,976,178 A | 11/1999 | Goldsteen et al. | | 6,309,416 B1 | 10/2001 | Swanson et al. |
| 5,984,871 A | 11/1999 | TenHoff et al. | | 6,328,689 B1 | 12/2001 | Gonzalez et al. |

| Patent Number | Date | Inventor |
|---|---|---|
| 6,336,933 B1 | 1/2002 | Parodi |
| 6,344,053 B1 | 2/2002 | Boneau |
| 6,371,964 B1 | 4/2002 | Vargas et al. |
| 6,394,956 B1 | 5/2002 | Chandrasekaran et al. |
| 6,428,550 B1 | 8/2002 | Vargas et al. |
| 6,440,163 B1 | 8/2002 | Swanson et al. |
| 6,488,673 B1 | 12/2002 | Laufer et al. |
| 6,490,474 B1 * | 12/2002 | Willis et al. .................. 600/424 |
| 6,514,249 B1 | 2/2003 | Maguire |
| 6,514,290 B1 | 2/2003 | Loomas |
| 6,533,812 B2 | 3/2003 | Swanson et al. |
| 6,585,655 B2 | 7/2003 | Crowley |
| 6,599,311 B1 | 7/2003 | Biggs et al. |
| 6,616,675 B1 | 9/2003 | Evard et al. |
| 6,623,437 B2 | 9/2003 | Hinchliffe et al. |
| 6,629,951 B2 | 10/2003 | Laufer et al. |
| 6,634,363 B1 | 10/2003 | Danek et al. |
| 6,692,494 B1 | 2/2004 | Cooper et al. |
| 6,712,804 B2 | 3/2004 | Roue et al. |
| 6,749,606 B2 | 6/2004 | Keast et al. |
| 6,770,070 B1 | 8/2004 | Balbierz |
| 6,970,733 B2 | 11/2005 | Willis et al. |
| 6,997,189 B2 | 2/2006 | Biggs et al. |
| 7,175,644 B2 | 2/2007 | Cooper et al. |
| 2001/0007940 A1 | 7/2001 | Hosheng et al. |
| 2001/0021872 A1 | 9/2001 | Bailey et al. |
| 2001/0047180 A1 | 11/2001 | Grudem et al. |
| 2002/0002401 A1 | 1/2002 | McGuckin, Jr. et al. |
| 2002/0022833 A1 | 2/2002 | Maguire et al. |
| 2002/0042564 A1 | 4/2002 | Cooper et al. |
| 2002/0042566 A1 | 4/2002 | Cooper et al. |
| 2002/0055772 A1 | 5/2002 | McGuckin, Jr. et al. |
| 2002/0087153 A1 | 7/2002 | Roschak et al. |
| 2002/0111619 A1 | 8/2002 | Keast et al. |
| 2002/0111620 A1 | 8/2002 | Cooper et al. |
| 2002/0128647 A1 | 9/2002 | Roschak |
| 2002/0138074 A1 | 9/2002 | Keast et al. |
| 2003/0070676 A1 | 4/2003 | Cooper et al. |
| 2003/0130657 A1 | 7/2003 | Tom et al. |
| 2004/0073155 A1 | 4/2004 | Laufer et al. |
| 2004/0073201 A1 | 4/2004 | Cooper |
| 2004/0211434 A1 | 10/2004 | Loomas et al. |
| 2004/0220556 A1 | 11/2004 | Cooper et al. |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0171527 A1 | 8/2005 | Bhola |
| 2005/0177144 A1 | 8/2005 | Phan et al. |
| 2005/0182475 A1 | 8/2005 | Jen et al. |
| 2005/0192526 A1 | 9/2005 | Biggs et al. |
| 2005/0228268 A1 | 10/2005 | Cole |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0123922 A1 | 5/2007 | Cooper et al. |

FOREIGN PATENT DOCUMENTS

| | | |
|---|---|---|
| EP | 0347098 A2 | 12/1989 |
| EP | 0443256 A1 | 8/1991 |
| JP | 2000-107178 | 4/2000 |
| JP | 2001-104315 | 4/2001 |
| WO | WO 89/06515 A1 | 7/1989 |
| WO | WO 90/01300 A1 | 2/1990 |
| WO | WO 95/02361 | 1/1995 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 A1 | 7/1998 |
| WO | WO 98/48706 | 11/1998 |
| WO | WO 99/01076 A1 | 1/1999 |
| WO | WO 99/11182 A1 | 3/1999 |
| WO | WO 99/25419 A1 | 5/1999 |
| WO | WO 99/60953 | 12/1999 |
| WO | WO 00/67825 | 11/2000 |
| WO | WO 00/72908 | 12/2000 |
| WO | WO 01/13839 | 3/2001 |
| WO | WO 01/28433 | 4/2001 |
| WO | WO 01/32088 | 5/2001 |
| WO | WO 01/70117 | 9/2001 |
| WO | WO 02/00278 | 1/2002 |

OTHER PUBLICATIONS

"Emphysema", National Heart, Lung, and Blood Institute. (pp. 1-5) (general information sheets on emphysema).

Panettieri, R.A. (1995). "Chronic Obstructive Pulmonary Disease" Chapter 6 In *Lippincott's Patholphysiology Series: Pulmonary Pathophysiology*. M.A. Grippi ed., J.B. Lippincott Company, Philadelphia, pp. 93-107.

* cited by examiner

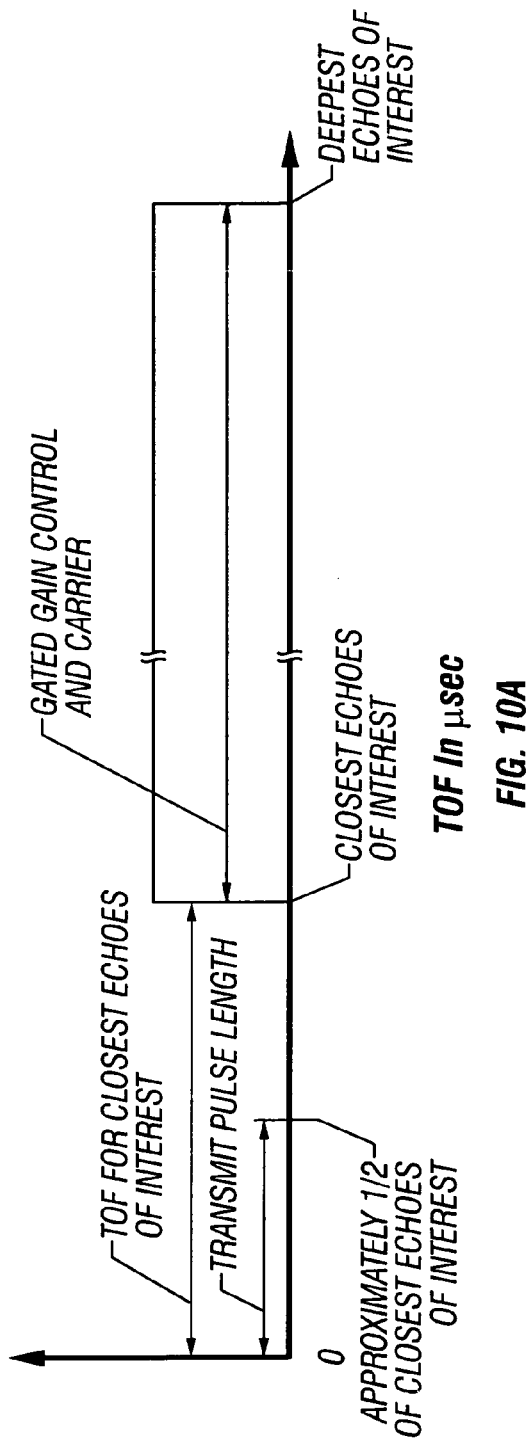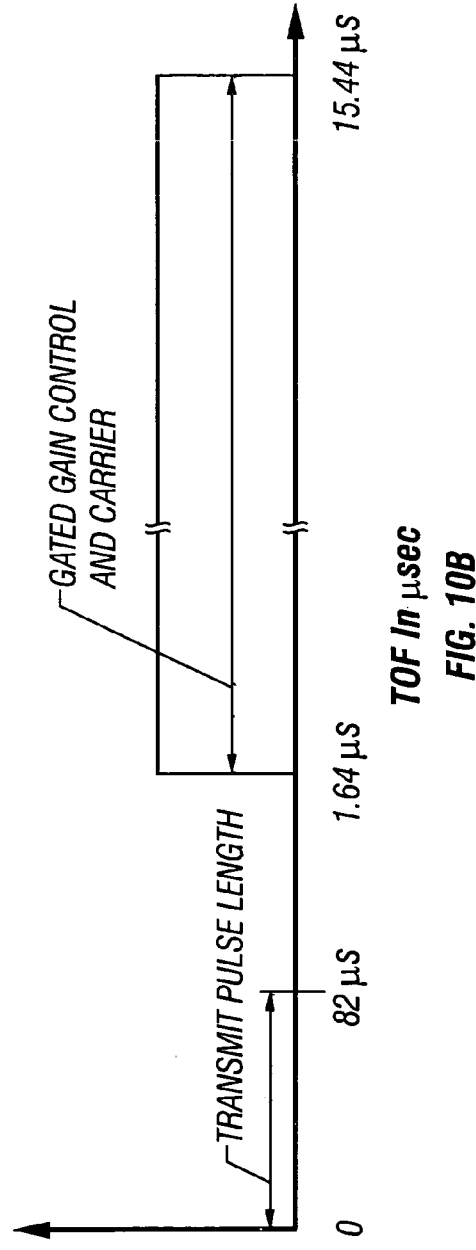

MULTIFUNCTIONAL TIP CATHETER FOR APPLYING ENERGY TO TISSUE AND DETECTING THE PRESENCE OF BLOOD FLOW

FIELD OF THE INVENTION

The invention is directed to devices for altering gaseous flow within a lung to improve the expiration cycle of an individual, particularly individuals having Chronic Obstructive Pulmonary Disease (COPD). More particularly, devices are disclosed to produce collateral openings or channels through the airway wall so that expired air is able to pass directly out of the lung tissue to facilitate both the exchange of oxygen ultimately into the blood and/or to decompress hyperinflated lungs.

BACKGROUND OF THE INVENTION

The term "Chronic Obstructive Pulmonary Disease" (COPD) is generally used to describe the disorders of emphysema and chronic bronchitis. Previously, COPD was also known as Chronic Obstructive Lung Disease (COLD), Chronic Airflow Obstruction (CAO), or Chronic Airflow Limitation (CAL). Some also consider certain types of asthma to fall under the definition of COPD. Emphysema is characterized by an enlargement of air spaces inside the lung. Hence, emphysema is an anatomic definition and it can only be presumed in a living patient. Chronic bronchitis is characterized by excessive mucus production in the bronchial tree. Chronic bronchitis is a clinical definition and denotes those individuals who meet criteria defining the disease. It is not uncommon for an individual to suffer from both disorders.

In 1995, the American Lung Association (ALA) estimated that between 15-16 million Americans suffered from COPD. The ALA estimated that COPD was the fourth-ranking cause of death in the U.S. The ALA estimates that the rates of emphysema is 7.6 per thousand population, and the rate for chronic bronchitis is 55.7 per thousand population.

Those inflicted with COPD face disabilities due to the limited pulmonary functions. Usually, individuals afflicted by COPD also face loss in muscle strength and an inability to perform common daily activities. Often, those patients desiring treatment for COPD seek a physician at a point where the disease is advanced. Since the damage to the lungs is irreversible, there is little hope of recovery. Most times, the physician cannot reverse the effects of the disease but can only offer treatment and advice to halt the progression of the disease.

To understand the detrimental effects of COPD, the workings of the lungs requires a cursory discussion. The primary function of the lungs is to permit the exchange of two gasses by removing carbon dioxide from venous blood and replacing it with oxygen. Thus, to facilitate this exchange, the lungs provide a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. Specifically, the airway begins with the trachea which branches into the left and right bronchi which divide into lobar, then segmental bronchi. Ultimately, the branching continues down to the terminal bronchioles which lead to the alveoli. Plates of cartilage may be found as part of the walls throughout most of the airway from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles are the smallest airways that do not contain alveoli. The function of the bronchi and bronchioles is to provide conducting airways that lead inspired air to the gas-blood interface. However, these conducting airways do not take part in gas exchange because they do not contain alveoli. Rather, the gas exchange takes place in the alveoli which are found in the distal most end of the airways.

The mechanics of breathing include the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric with respect to the pressure at the airway openings. Consequently, air flows into the lungs causing the lungs to expand. During unforced expiration, the expiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed the pressure at airway openings causing air to flow out of the lungs and deflate the lungs. If the lungs' ability to recoil is damaged, the lungs cannot contract and reduce in size from their inflated state. As a result, the lungs cannot evacuate all of the inspired air.

In addition to elastic recoil, the lung's elastic fibers also assist in keeping small airways open during the exhalation cycle. This effect is also known as "tethering" of the airways. Such tethering is desirable since small airways do not contain cartilage that would otherwise provide structural rigidity for these airways. Without tethering, and in the absence of structural rigidity, the small airways collapse during exhalation and prevent air from exiting thereby trapping air in within the lung.

Emphysema is characterized by irreversible biochemical destruction of the alveolar walls that contain the elastic fibers, called elastin, described above. The destruction of the alveolar walls results in a dual problem of reduction of elastic recoil and the loss of tethering of the airways. Unfortunately for the individual suffering from emphysema, these two problems combine to result in extreme hyperinflation (air trapping) of the lung and an inability of the person to exhale. In this situation, the individual will be debilitated since the lungs are unable to perform gas exchange at a satisfactory rate.

One further aspect of alveolar wall destruction is that the airflow between neighboring air sacs, known as collateral ventilation or collateral air flow, is markedly increased as when compared to a healthy lung. While alveolar wall destruction decreases resistance to collateral ventilation, the resulting increased collateral ventilation does not benefit the individual since air is still unable to flow into and out of the lungs. Hence, because this trapped air is rich in CO2, it is of little or no benefit to the individual.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD. Moreover, patients requiring a supplemental source of oxygen are usually never able to return to functioning without the oxygen.

Lung volume reduction surgery is a procedure which removes portions of the lung that are over-inflated. The improvement to the patient occurs as a portion of the lung that remains has relatively better elastic recoil which allows for reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the long term benefits of this surgery are still being evaluated. In any case, it is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung increases the cavity area in which the non-diseased parenchyma may expand and contract. If the entire lung were emphysematous, the parenchyma is less elastic and cannot expand to take advantage of an increased area within the lung cavity.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous.

The present invention addresses the problems caused by COPD by providing a device configured to create collateral openings through an airway wall which allows expired air to pass directly out of the lung tissue responsible for gas exchange. These collateral openings ultimately decompress hyper inflated lungs and/or facilitate an exchange of oxygen into the blood.

Furthermore, there is also a need for devices that are able to access remote areas of the body to provide dual functions of locating an acceptable site for removal or cutting of tissue and then removing or cutting the tissue without having to reposition the device. Such a need is evident in dynamically moving environments (e.g., the lungs) where repositioning of a device to find the original target site may be difficult.

Doppler ultrasound is an effective means to determine the presence or absence of a blood vessel within tissue. It is known that sound waves at ultrasonic frequencies travel through tissue and reflect off of objects/interfaces where density gradients exist. In such a case, the reflected signal and the transmitted signal will have the same frequency. Alternatively, in the case where the signal is reflected from the blood cells moving through a blood vessel, the reflected signal will have a shift in frequency from the transmitted signal. This shift is known as a Doppler shift. However, since the characteristics of components used to detect a Doppler shift vary from characteristics of components used to cut or remove tissue, it is difficult to cut or remove tissue in precisely the same location and immediately after detection has taken place. It is usually required that the component or device used to detect any Doppler shift first must be moved to allow a second component or device to cut or remove the tissue at the same precise location. For instance, if a device uses energy to create an opening or ablate tissue, the energy delivery components may not have acceptable characteristics to function as Doppler components. Furthermore, the process of delivering energy through the device may undesirably impact any Doppler components.

When using Doppler in tissue it is noted that the acoustic impedance of the ultrasound transducer and the acoustic impedance of tissue differ significantly. As a result, the ultrasound signal may experience significant reflection and divergence at the tissue/transducer interface. To address this issue, a tip or lens may be used as an interface between the transducer and tissue.

In common Doppler ultrasound applications, a tip material is selected to provide an optimum acoustic match between the ultrasonic transducer and tissue. This optimum acoustic match is the geometric mean impedance between the tissue and the transducer material, governed by the following equation.

$$Z_{optimum} = (Z_{tissue} \times Z_{transducer})^{1/2}$$

Where $Z_{optimum}$ is the desired acoustic impedance of the tip material; $Z_{tissue}$ is the acoustic impedance of tissue; and $Z_{transducer}$ is the acoustic impedance of the transducer. Generally, $Z_{tissue}$ ranges from 1.38 MRayls (for fat) to 1.70 MRayls (for muscle), while $Z_{transducer}$ is approximately 30 MRayls for ceramic transducer materials. Therefore, using $Z_{transducer}$ of 1.54 MRayls (the average acoustic impedance for tissue) the desirable tip material should have an acoustic impedance around 6.79 MRayls.

Most materials having an acoustic impedance close to this range are made of epoxy composites and range from, for example, 1.78 MRayls for a methylpentene copolymer (e.g., TPX, Matsui Plastics, White Plains, N.Y.) to 4.39 MRayls for high temperature plastics (e.g., CELAZOLE, Curbell Plastics, Glenshaw, Pa.).

One drawback to using Doppler ultrasound devices for placing collateral openings in tissue is that conventional tip materials selected for their desirable acoustic impedance are not effective to deliver energy (e.g., RF, resistive heat, etc.) The acoustic impedance of electrically and thermally conductive materials is higher than the desired acoustic impedance of 6.79 MRayls. For example, $Z_{aluminum}$ is approximately 18 MRayls, $Z_{titanium}$ is approximately 27 MRayls, and $Z_{stainless\ steel}$ is approximately 45 MRayls.

Another drawback to delivering energy through devices configured for Doppler applications is that the transducer is prone to being damaged. For example, when used to deliver therapeutic RF energy, an electrically conductive tip experiences heating. If a sufficient amount of heat is conducted from the tip, the transducer may depolarize. Moreover, conduction of heat through the device may adversely affect the joints and bonds between the transducer, tip and device. As a result, there is the potential of a catastrophic failure of the device if the assembly breaks apart during use in the body.

In view of the above, the present invention provides a device capable of locating an acceptable site for the creation of a collateral opening and then creating an opening in the tissue using a device capable of both functions. While the present invention is discussed as having applicability to creation of collateral openings it was found to have utility for other applications as well. For example, the present invention is suited for the application of energy to tissue in a safe manner (e.g., tumor ablation, tissue removal, application of heat to structures within the body, etc.). Especially when there is a need to avoid blood vessels, or other tissue/organs/structures. The invention has applicability given a need to use of Doppler effect to locate movement within tissue and then apply energy based on the observation of the Doppler effect.

Methods and devices for creating, and maintaining collateral channels are also discussed in U.S. patent application Ser. No. 09/633,651, filed on Aug. 7, 2000; U.S. patent application Ser. Nos. 09/947,144, 09/946,706, and 09/947,126 all filed on Sep. 4, 2001; U.S. Provisional Application No. 60/317,338 filed on Sep. 4, 2001, and 60/334,642 filed on Nov. 29, 2001, whereas the entirety of each listed application is incorporated by reference herein.

SUMMARY OF THE INVENTION

The invention related to devices for applying energy to tissue. The invention includes an elongate member having a proximal portion and a distal portion; a transducer assembly located towards the distal portion of the elongate member, and an electrically conductive tip located at a distal end of the elongate member adjacent to the transducer assembly and having a front and back surface, the back surface being in acoustical communication with the transducer assembly wherein the tip is adapted to communicate a source signal from the transducer assembly out through the front surface, the tip also being adapted to communicate a reflected signal from the front surface to the transducer; and at least two conducting members extending through at least a portion of the elongate member, at least one of the conducting members capable of electrically coupling an RF energy supply to the tip.

The tip of the device functions to direct signals to and from the transducer assembly as well as conduct electro-surgical energy (e.g., RF energy) to desired areas. As such, to accommodate the nature of electrically conductive materials so that they function as an acceptable Doppler tip, variations of the invention include tips that have a length selected from a multiple of one quarter of a wavelength of the source signal.

The invention further includes transducer assemblies wherein the transducer assembly comprises a covering having a proximal and distal end, at least one transducer having at least a first and second pole, at least a portion of the transducer being located within the covering, a first conductive medium in contact with the first pole of the transducer and extending to at least a portion of an outer surface of the covering, and wherein at least a first of the conducting members is electrically coupled to the first conductive medium, and a second of the conducting members extends through the proximal end of the covering and electrically couples to the second pole of the transducer.

The invention may include insulating layers that serve to protect tissue and/or parts of the device from unwanted heating. The elongate member of the device may also serve as the insulating layer or as additional insulation.

The invention also includes a transducer assembly that is configured to minimize the size of the device so that it may access deeper regions of the body (e.g., deeper regions of airways in the lungs). The transducer assembly may include a covering that is either conductive or is covered by a conductive medium. As such, the covering (or conductive medium) provides an electrical path to a pole of the transducer, thereby eliminating the need for a separate electrical connection. The conductive covering (or conductive medium) may optionally be used as an electrical path to a conductive tip.

The invention also includes a medical device for detecting Doppler shift and for applying energy to tissue, the medical device comprising an elongate member having a proximal portion and a distal portion; a transducer means (e.g., a transducer assembly as described herein) for generating a source signal and for receiving a reflected signal wherein the transducer means is located towards the distal portion of the elongate member; a directing means (e.g., a tip as described herein) for directing the source signal and the reflected signal, the signal directing means located at a distal end of the distal portion of the elongate member and being in acoustical communication with the transducer means, and a first conducting member and a second conducting member both extending through at least a portion of the elongate member, the conducting members electrically coupled to at least the transducer assembly.

The signal directing means described above may also be adapted to direct or deliver energy to tissue.

The invention also includes methods of locating a site to apply energy to tissue and applying energy to tissue. These methods include generating a source signal with a transducer, transmitting the source signal through an electrically conductive electrode to the tissue, receiving a reflected signal, determining any difference in frequency between the source signal and reflected signal, and applying energy to tissue using the electrically conductive electrode. In the present invention, the electrically conductive tip may serve as the electrically conductive electrode.

The methods include receiving the reflected signal through the electrically conductive electrode. The electrically conductive electrode may comprise a material selected from the group consisting of aluminum, titanium, stainless steel. Or, the electrically conductive electrode may comprise a non-electrically conductive material coated with an electrically conductive material.

The methods include generating the source signal using pulsed wave ultrasound. In such a case the source signal may have a pulse length equal to or less than (preferably half of) the time required for the reflected signal to return from a first area of interest.

The method includes determining any difference in frequency between the source signal and reflected signal starting at the time required for the reflected signal to return from the first area of interest and ending at the time required for the reflected signal to return from a second area of interest. In such cases, the first and second areas of interest may include the range of depth of penetration for determining the Doppler effect.

The invention includes kits containing the inventive device with any one or more of the following components, an RF energy supply, a Doppler ultrasound controller, a conduit as described in one or more of the applications listed herein, and a bronchoscope/endoscope.

BRIEF DESCRIPTION OF THE DRAWINGS

FIGS. 10A-10B illustrate time-of-flight diagrams for the Doppler echo signal used to determine the Doppler control settings.

DETAILED DESCRIPTION OF THE INVENTION

Figure 1A:
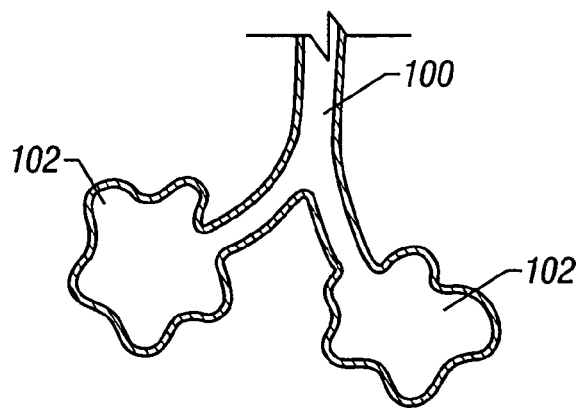
FIGS. 1A-1C illustrate various states of the natural airways and the blood-gas interface.
Figure 1B:
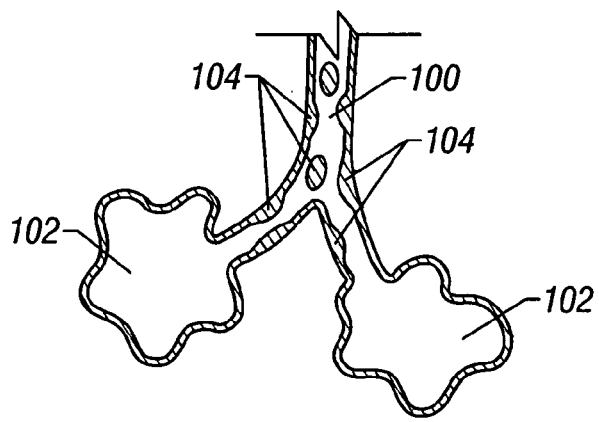
Figure 1C:
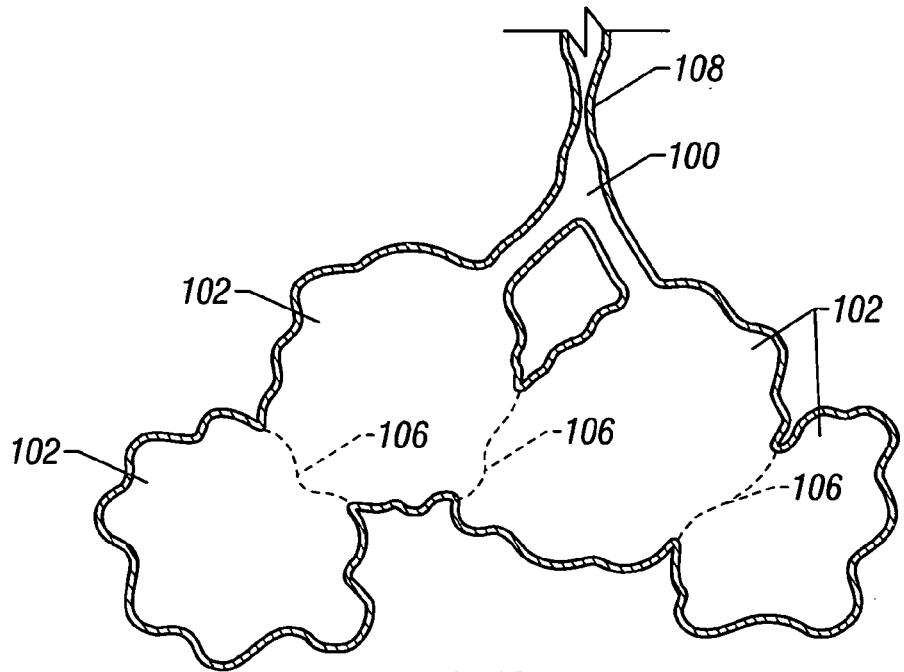

Prior to considering the invention, simplified illustrations of various states of a natural airway and a blood gas interface found at a distal end of those airways are provided in FIGS. 1A-1C. FIG. 1A shows a natural airway 100 which eventually branches to a blood gas interface 102. FIG. 1B illustrates an airway 100 and blood gas interface 102 in an individual having COPD. The obstructions 104 (e.g., excessive mucus resulting from COPD, see above) impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. More usually, the states of the lung depicted in FIGS. 1B and 1C are often found in the same lung.

The following illustrations are examples of the invention described herein. It is contemplated that combinations of aspects of specific embodiments/variations or combinations of the specific embodiments/variations themselves are within the scope of this disclosure.

As will be explained in greater detail below, the production and maintenance of collateral openings or channels through airway walls permits expired air to pass directly out of the lung tissue and into the airways to ultimately facilitate exchange of oxygen into the blood and/or decompress hyper inflated lungs. The term 'lung tissue' is intended to include the tissue involved with gas exchange, including but not limited to, gas exchange membranes, alveolar walls, parenchyma and/or other such tissue. To accomplish the exchange of oxygen, the collateral channels allow fluid communication between an airway and lung tissue. Therefore, gaseous flow is improved within the lung by altering or redirecting the gaseous flow within the lung, or entirely within the lung.

Figure 1D:
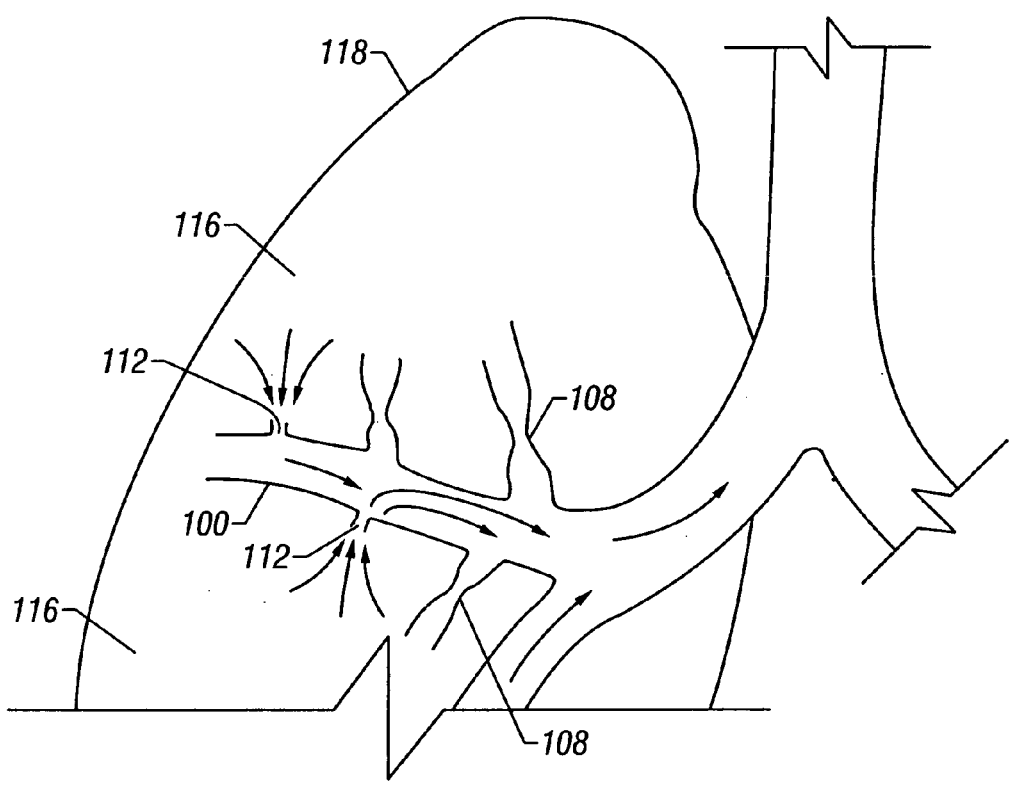
FIG. 1D illustrates a schematic of a lung demonstrating a principle of the effect of collateral channels placed therein.

FIG. 1D illustrates a schematic of a lung 118 to demonstrate a benefit of the production and maintenance of collateral openings or channels through airway walls. As shown, a collateral channel 112 (located in an airway wall 110) places lung tissue 116 in fluid communication with airways 100 allowing expired air to directly pass out of the airways 100. The term channel is intended to include an opening, cut, slit, tear, puncture, or any other conceivable artificially created opening. As shown, constricted airways 108 may ordinarily prevent air from exiting the lung tissue 116. In the example illustrated in FIG. 1D, there is no implanted structure placed in the collateral channel 112. However, conduits (not shown) may be placed in the collateral channels 112 to assist in maintaining the patency of the collateral channels 112. Examples of conduits may be found in the applications discussed above. While there is no limit to the number of collateral channels which may be created, it is preferable that 1 or 2 channels are placed per lobe of the lung. For example, the preferred number of channels is 2-12 channels per individual patient. In current trials, it was found that 1-4 channels placed per lobe of the lung and 4-16 channels per individual patient was preferable. This number may vary on a case by case basis. For instance, in some cases an emphysematous lung may require 3 or more collateral channels in one or more lobes of the lung.

In the following explanation of figures, similar numerals may represent similar features for the different variations of the invention. The invention herein is described by examples and a desired way of practicing the invention is described. However, the invention as claimed herein is not limited to that specific description in any manner. Equivalence to the description as hereinafter claimed is considered to be within the scope of protection of this patent.

The devices of the present invention are configured to locate a target site for creation of a collateral channel in the tissue and to create an opening in tissue. As discussed above, a benefit of this combination feature is that a single device is able to select a target location and then create an opening without having been moved. Although the device is discussed as being primarily used in the lungs, the device is not limited as such and it is contemplated that the invention has utility in other areas as well, specifically in applications in which blood vessels or other structures must be avoided while cutting or removing tissue (one such example is tumor removal.)

The present invention includes the use of a device which is able to detect the presence or absence of a blood vessel by placing a front portion of the device in contact with tissue. One variation of the invention includes the use of Doppler ultrasound to detect the presence of blood vessels within tissue. However, the frequency of the signals is not limited to the ultrasonic range, for example the frequency may be within the range of human hearing, etc.

The ultrasound Doppler operates at any frequency in the ultrasound range but preferably between 2 Mhz-30 Mhz. It is generally known that higher frequencies provide better resolution while lower frequencies offer better penetration of tissue. In the present invention, because location of blood vessels does not require actual imaging, there may be a balance obtained between the need for resolution and for penetration of tissue. Accordingly, an intermediate frequency may be used (e.g., around 8 Mhz). A variation of the invention may include inserting a fluid into the airway to provide a medium for the Doppler sensors to couple to the wall of the airway to detect blood vessels. In those cases where fluid is not inserted, the device may use mucus found within the airway to directly couple the sensor to the wall of the airway.

Figure 2A:
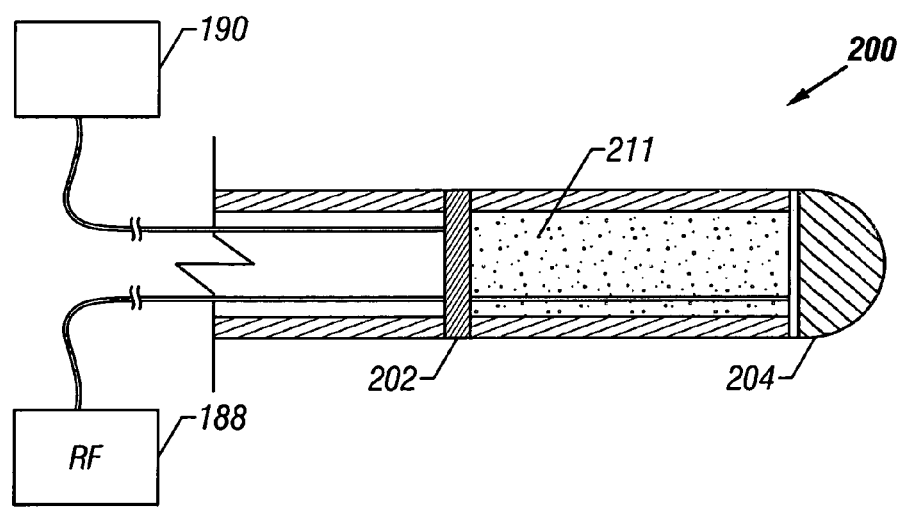
FIGS. 2A-2C are side views of variations of the invention having an electrically conductive tip which is able to function as a Doppler tip as well as create the collateral channels.

FIG. 2A illustrates a variation of a device 200 of the present invention where a tip 204 of the device has a conductive portion, (e.g., is made from a conductive material or has a conductive coating) allowing the tip to serve as both an acoustic lens and an RF electrode. Accordingly, the tip 204 is connected to an RF generator 188 for creating channels within tissue and a transducer assembly 202 is placed in communication with an analyzing device 190 that is adapted to measure the Doppler shift between generated and reflected signals. It is contemplated that, throughout this disclosure, the transducer assembly 202 may be a transducer or a transducer coupled with a covering and other components. In this variation, the tip 204 may be separated from the transducer 202, but both the tip 204 and transducer 202 are in acoustic communication through the use of a separation medium 211. The separation medium 211 transmits signals between the tip 204 and the transducer 202. In some variations of the invention, the spacing of the transducer 202 from the tip 204 serves to prevent heat or RF energy from damaging the transducer 202. It is intended that the spacing between the transducer 202 and tip 204 shown in the figures is for illustration purposes only. Accordingly, the spacing may vary as needed. The separation medium must have acceptable ultrasound transmission properties and may also serve to provide additional thermal insulation as well. For example, an epoxy as describe herein, may be used for the separation medium.

It is also contemplated that the inventive device may create openings in tissue using any type of energy capable of removing/ablating tissue. For example, either RF energy, or a focused ultrasound may be used.

Figure 2B:
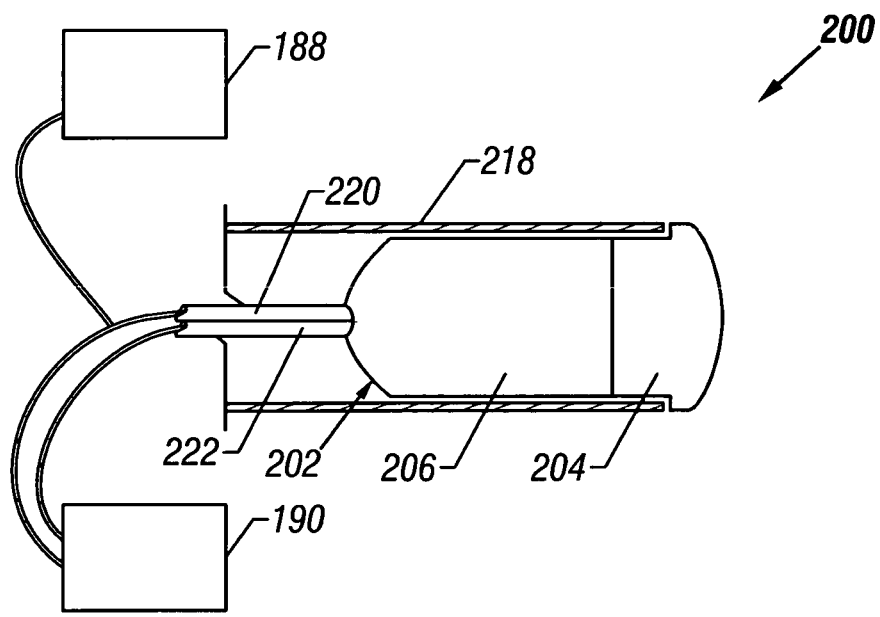

FIG. 2B illustrates a sectional side view of a variation of the inventive device 200. The device 200 includes a transducer assembly 202. As shown in the figure, an electrically conductive tip 204 is adjacent to the transducer assembly 202 and at a distal end of the elongate member 218. The transducer assembly 202 is located towards a distal portion of the elongate member 218. The transducer assembly of any variation of the present invention may be located within the elongate member, or it may be located within a portion of the tip of the device. In any case, the transducer assembly will be located towards the distal portion of the elongate member. The elongate member 218 of the present invention may or may not have a lumen extending therethrough. The elongate member described herein may be comprised of any commercially available medical-grade flexible tubing. Furthermore, the elongate member may be selected from material that provides insulation from the heat generated by the device. For example, the elongate member may comprise a PTFE material. In such cases, the elongate member will provide insulation for tissue that is adjacent to the area where creation of a collateral channel is desired. Also, in some cases, insulation may be required to prevent damage to the transducer assembly.

The device 200 further includes a first conducting member 220 and a second conducting member 222 (e.g., wires) both extending through at least a portion of elongate member 218 to the transducer assembly 202. The conducting members 220, 222 may extend through a lumen of the elongate member 218 or may extend in the wall of the elongate member 218. In any case, the conducting members 220, 220 provide the energy and controls for the transducer assembly 202. For example, the conducting members 220, 222 may be coupled to an ultrasound source 190. Moreover, variations of the inventive device include conducting members 220, 222 which may be comprised of a series of wires, with one set of wires being coupled to respective poles of the transducer, and any number of additional sets of wires extending through the device. Ultimately, the wires enable the device to couple to energy and control units. Although not illustrated, the device 200 may also include an outer sheath (not shown in FIG. 2B) in which the device 200 may be advanced to a target tissue site.

Figure 2C:
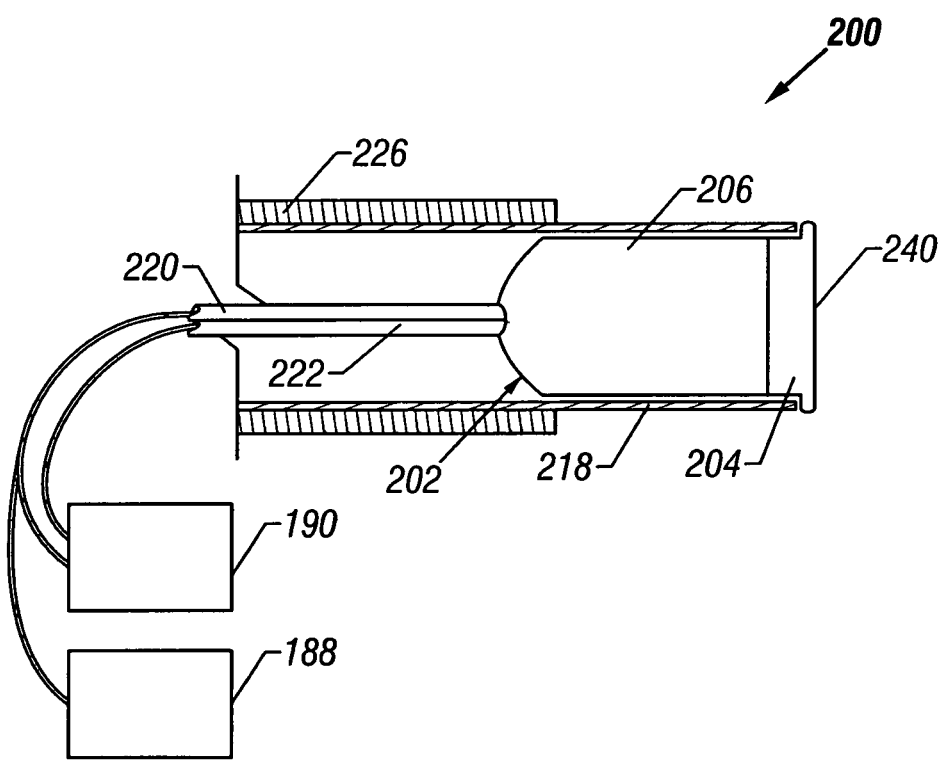

FIG. 2C illustrates another variation of a device 200 for creating collateral channels. In this variation, a transducer assembly 202 is provided with a conductive tip 204 having a flatter front surface 240. It should be noted that the shape of the tips illustrated in FIGS. 2A-2C are intended to illustrate examples of tips for the present invention, the shapes of the tips are not meant to be limited to any particular variation of the device. The tip 204 is located adjacent to a covering 206 of the transducer assembly 202. The transducer assembly 202 is located towards a distal portion of the elongate member 218. In the variation depicted in FIG. 2C the device 200 also includes an (optional) outer sheath 226. As illustrated, the conductive tip 204 may be coupled to an energy source 188 using one of the conducting members 220 or 222. In such a case, the tip 204 will be electrically coupled to one of the conducting members.

Although the transducer assembly is adapted to generate a source signal and receive a reflected signal, variations of the invention may omit the transducer covering and other structures not necessary to generate a source signal and receive a reflected signal. Therefore, it is contemplated that the invention may simply have a transducer that is coupled to a controller.

FIGS. 3A-3D, illustrate possible variations of the tip 204 of the device. It is noted that these variations are provided for illustrative purposes and are not meant to be exhaustive. The tips 204 of the present invention may function as a lens to disperse and/or direct a signal over a substantial portion of the outer surface of the tip 204. The tip 204 also is adapted to disperse and/or direct (e.g., by diffraction) a reflected signal towards the transducer (not shown in FIGS. 3A-3D). Accordingly, given the above described configuration, the inventive device 200 will be able to detect vessels with substantially most of the tip 204. Because most of the tip 204 is able to direct a signal to and from the transducer 208, this device 200 may detect vessels through a greater range of motion (e.g., as opposed to requiring the device 200 to be orthogonal to the tissue.) Furthermore, the tip may comprise a directing means.

The tip 204 is designed such that it interferes and redirects the signals in a desired direction in a manner like a lens. It also may be desirable to place an epoxy between the tip 204 and the transducer. Preferably, the epoxy is thin and applied without air gaps, bubbles or pockets. Also, the density/hardness of the epoxy should provide for transmission of the signal while minimizing any effect or change to the source signal. The configuration of the transducer assembly 202 permits the tip 204 to disperse a signal over a substantial portion of its outer surface 240. The tip 204 also is adapted to refract a reflected signal towards the transducer 208. Accordingly, given the above described configuration, the inventive device will be able to detect vessels with any part or substantially all of the lens 204 that contacts tissue.

Although the tip is of the present invention is able to transmit a source signal and receive a reflected signal, the invention is not limited to requiring both functions. For example, the inventive device could be configured to generate a source signal and direct the source signal to an area of interest but a second device or transducer assembly could be used to receive the reflected signal. Accordingly, a separate device could be used to generate the source signal with the inventive device being used to receive the reflected signal.

The invention contemplates the tip 204 as comprising an electrically conductive material such that energy (e.g., RF energy or thermal energy) may be delivered to the tissue via the tip 204. For example, the tip may comprise titanium, aluminum, or stainless steel, etc. any electrically conductive metal. Also, the tip 204 may be comprised of any material suitable for ultrasound applications but is not particularly electrically conductive. In such a case, the tip will have an electrically conductive coating about at least a portion of the tip. These tip materials include dimethyl pentene, a methylpentene copolymer (plastic-TPX), carbon aerogel, polycarbonate (e.g., Lexan), polystyrene, etc. (e.g., any standard material used for ultrasound applications.) Electrically conductive coatings include gold, silver, tantalum, copper, chrome, or any bio-compatible electrically conductive material, etc. This material may be coated, deposited, plated, painted, wound, wrapped (e.g., a conductive foil), etc. onto the tip 204.

As discussed above, traditional tip materials are selected to provide an optimum acoustic match between the ultrasonic transducer and tissue. Use of such electrically conductive materials do not provide optimum acoustic impedance in Doppler applications. To overcome the problem associated with tip materials having undesirable acoustic impedance, the tip 204 of the present invention is selected to be long enough to avoid excessive heating of the transducer 208 and at a length that minimizes the signal clutter resulting from the use of material.

In view of the above, a tip 204 length is selected in accordance with the following equation:

$$L = N(\lambda/4) \text{ for } Z\text{transducer} > Z\text{tip} > Z\text{tissue}$$

Where L=tip length; N=any integer; and λ=wavelength of the signal. It was found that the best performance was obtained by selecting a tip length where N is an odd integer. This minimizes the destructive interference of the signal caused by echoes reverberating within the tip. It was also found that while N=1 was acceptable for the Doppler function, the resulting tip length caused undesirable heating of the transducer. To achieve a balance of a tip length that would prevent unacceptable heating of the transducer, N was chosen to be 7 for one variation of the device. Accordingly, an acceptable length for a titanium tip corresponding to a frequency of 8 Mhz, equals 1.33 mm or 0.052 in.

Figure 3D:
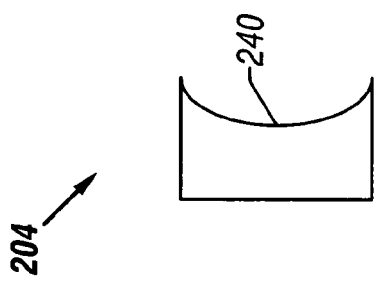
FIGS. 3A-3D illustrate examples of tip configurations of the present invention.
Figure 3C:
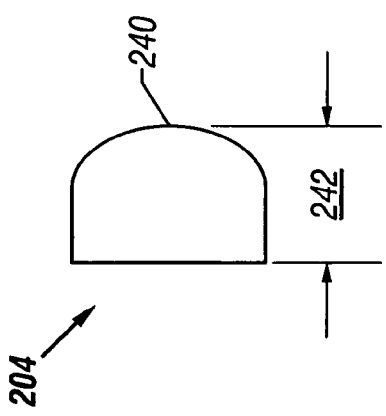
Figure 3B:
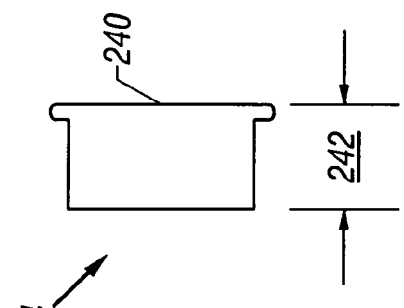
Figure 3A:
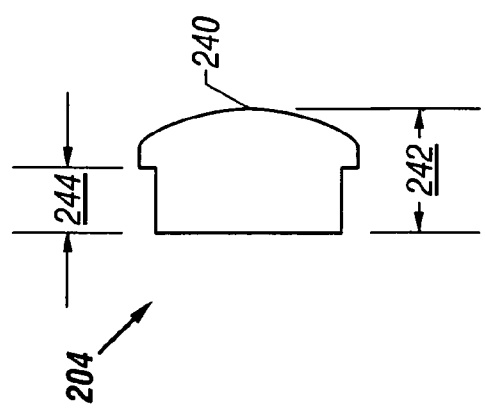

A measurement of the tip lengths 242 may be seen in FIGS. 3A-3D. FIG. 3A illustrates a variation of the tip 204 having a rounded front surface 240. In this case, the tip length 242 of the entire tip may be selected such that N is an odd integer (e.g., 9) and the length behind the front surface 244 may be selected to be any integer multiple of the wavelength (e.g., 6 or 7). In such an example the length of 242 may be selected, for example, $L_{242}=9(\lambda/4)$ and $L_{244}=7(\lambda/4)$.

As illustrated in FIG. 3A, although the front surface 240 of the tip 204 is illustrated as being hemispherical, the tip 204 may have other profiles as well. For example, it is desirable that the tip 204 produce a certain amount of divergence of the signal being passed therethrough. However, depending on a variety of factors (e.g., material, frequency of the signal, etc.) a tip 204 may encounter excessive divergence which is destructive to the outgoing signal. Accordingly, it may be desirable to produce a tip 204 as illustrated in FIG. 3B in which a front surface 240 of the tip 204 is substantially flat. The degree of flatness of the tip 204 will often depend upon experimentation to reduce the amount of destructive reflections, thus minimizing excessive divergence due to differences in speed of sound in tip versus tissue. Use of a materials with higher acoustical impedance, such as titanium and stainless steel, may require a flatter tip due to the resulting divergence of the source signal. FIG. 3C illustrates another variation of a tip 204 having a rounded front surface 240 but with no projections on the sides of the tip 204. FIG. 3D illustrates a tip 204 with a concave front surface 240.

It may also be desirable that the device is configured such that there are no exposed sharp edges that may cause any unintended damage to tissue while the device is being used to determine the presence or absence of a blood vessel. In such a case, for example, the tip may be designed such that it doesn't have sharp edges, or any sharp edges may be covered by other parts of the device (e.g., the elongate member, an outer sheath, etc.)

As discussed herein, for some variations of the invention it is desirable to minimize the size of the device especially at the distal end. Although the invention may be any size, it was found that an overall device diameter of 0.071" was acceptable. As noted, because the device is advanced through the airways, the device may treat deeper areas in the airways of the lungs given a smaller outside diameter of the distal end of the device. This size also permits delivery of the device into the lungs through the working channel of a standard bronchoscope or endoscope. However, this reduction in size is limited as functionality of the device may suffer. For example, one or more wires will be selected such that they will deliver sufficient RF energy over a desired period of time without experiencing unacceptable heating. Therefore, the smallest acceptable cross sectional area of a single wire or multiple wires will be a balance of the energy delivery requirements of the device versus the characteristics of the wire or wires.

Figure 4A:
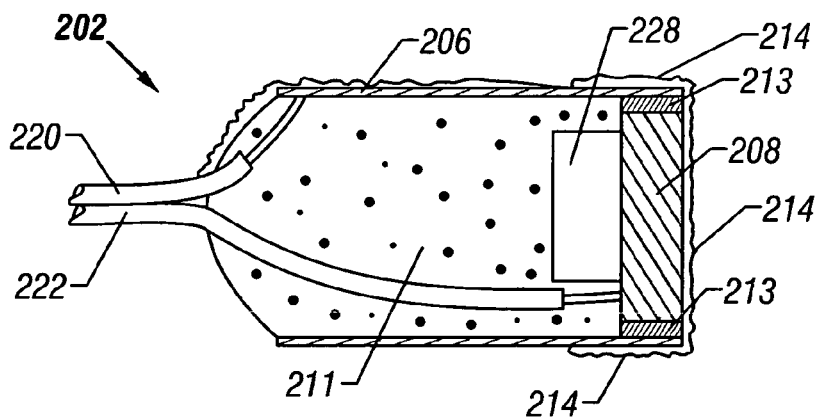
FIGS. 4A-4B illustrate cross sectional views of examples of transducer assemblies of the present invention.
Figure 4B:
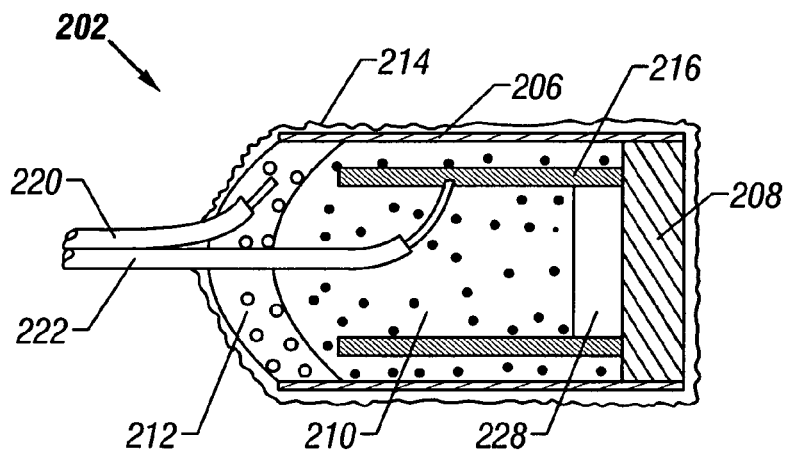

FIGS. 4A-4B illustrate variations of the transducer assembly 202 which are configured to reduce an overall size of the assembly. FIG. 4A illustrates a cross-sectional view of a basic variation of a transducer assembly 202 for use with the present invention. For illustration purposes, the transducer assembly 202 illustrated in FIG. 4A is shown without a tip. The transducer assembly 202 includes at least one transducer 208 (e.g., a piezoelectric transducer.) In this variation, the front surface of the transducer 208 comprises a first pole and the rear surface comprises a second pole.

The transducer or transducers may comprise a piezo-ceramic crystal (e.g., a Motorola PZT 3203 HD ceramic). In the current invention, a single-crystal piezo (SCP) is preferred, but the invention does not exclude the use of other types of ferroelectric material such as poly-crystalline ceramic piezos, polymer piezos, or polymer composites. The substrate, typically made from piezoelectric single crystals (SCP) or ceramics such as PZT, PLZT, PMN, PMN-PT; also, the crystal may be a multi layer composite of a ceramic piezoelectric material. Piezoelectric polymers such as PVDF may also be used. Micromachined transducers, such as those constructed on the surface of a silicon wafer are also contemplated (e.g., such as those provided by Sensant of San Leandro, Calif.) As described herein, the transducer or transducers used may be ceramic pieces coated with a conductive coating, such as gold. Other conductive coatings include sputtered metal, metals, or alloys, such as a member of the Platinum Group of the Periodic Table (Ru, Rh, Pd, Re, Os, Ir, and Pt) or gold. Titanium (Ti) is also especially suitable. The transducer may be further coated with a biocompatible layer such as Parylene or Parylene C.

The covering 206 of the transducer assembly 202 contains the transducer 208. In some variations of the invention, the covering 206 may comprise a conductive material. In such cases the covering 206 itself becomes part of the electrical path to the first pole of the transducer 208. Use of a conductive covering 206 may require insulating material 213 between the sides of the transducer 208, thereby permitting a first conductive medium 214 to electrically couple only one pole of the transducer 208 to the covering 206.

At least a portion of the front surface of the transducer 208, will be in contact with the conductive medium 214. The conductive medium 214 permits one of the poles of the transducer 208 to be placed in communication with a conducting member that is ultimately coupled to a power supply. As shown in this example, the conductive medium 214 places the pole of the transducer 208 in electrical communication with the covering 206. In some variations the conductive medium 214 may coat the entire transducer 208 and covering 206. Alternatively, the conductive medium 214 may be placed over an area small enough to allow for an electrical path between a conducting member and the respective pole of the transducer 208. The conductive medium 214 may be any conductive material (e.g., gold, silver, tantalum, copper, chrome, or any bio-compatible conductive material, etc. The material may be coated, deposited, plated, painted, wound, wrapped (e.g., a conductive foil), etc. onto the transducer assembly 202.

The transducer assembly 202 depicted in FIG. 4A also illustrates conducting members 220, 222 electrically coupled to respective poles of the transducer 208. Optionally, the conducting members 220, 222 may be encapsulated within an epoxy 211 located within the covering 206. The epoxy 211 may extend to the transducer 208 thereby assisting in retaining both the conducting members 220, 222 and transducer 208 within the covering. It may also be desirable to maintain a gap 228 between the transducer 208 and any other structure. It is believed that this gap 228 improves the ability of the transducer assembly 202 to generate a signal.

FIG. 4B illustrates another variation of a transducer assembly 202. In this variation, the conductive medium 214 extends over the entire transducer covering 206. Accordingly, the covering 206 may be made of a non-conducting material (e.g., a polyamide tube, polyetherimide, polycarbonate, etc.) The transducer assembly 202 may further comprise a second tube 216 within the covering 206. This second tube 216 may be a hypo-tube and may optionally be used to electrically couple one of the conducting members to a pole of the transducer 208. As shown, the covering 206 may contain a non-conductive epoxy 210 (e.g., Hysol 2039/3561 with Scotchlite glass microspheres B23/500) which secures both the conducting member and the second tube 216 within the covering 206. This construction may have the further effect of structurally securing the transducer 208 within the assembly 202. Again, a gap 228 may or may not be adjacent to the transducer to permit displacement of the transducer 208.

FIG. 4B also illustrates the assembly 202 as having a conductive epoxy 212 which encapsulates the alternate conducting member 220. An example of a conductive epoxy is Bisphenol epoxy resin with silver particulates to enable conductivity. The particulates may be from 70-90% of the resin composition. The resin may then be combined with a hardener (e.g., 100 parts resin per 6 parts hardener.) The conductive epoxy 212 is in electrical communication with the conductive medium 214 allowing for a conductive path from the conducting member 220 to the conductive medium 214. Accordingly, use of the conductive epoxy 212 secures the conducting member 220 to the assembly 202 while electrically coupling the conducting member 220 to the transducer via the conductive coating 214.

Figure 5A:
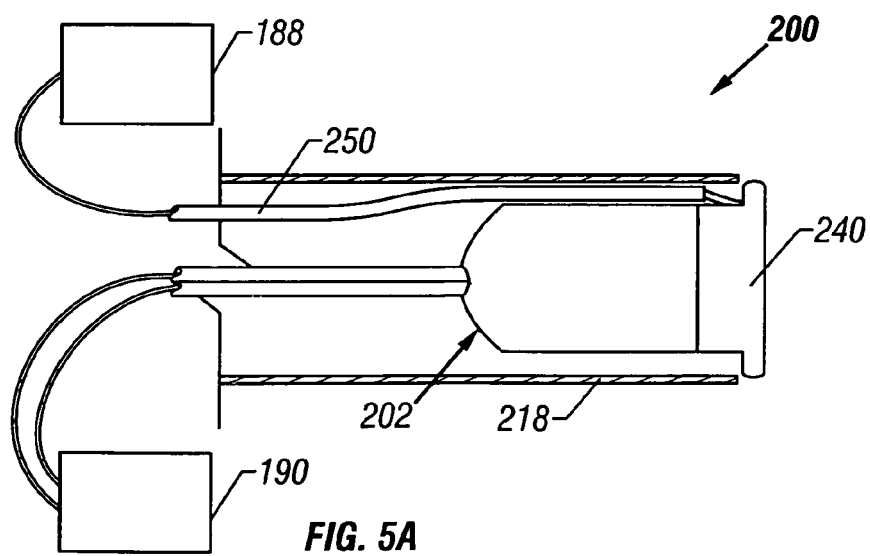
FIGS. 5A-5E illustrate various configurations used to deliver energy to the tip of the inventive device.
Figure 5B:
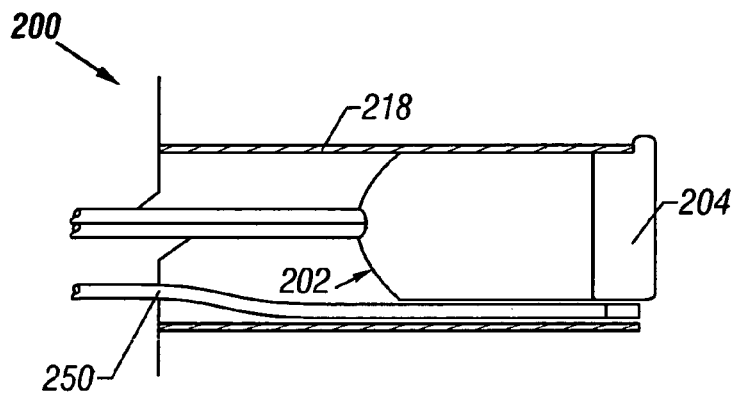
Figure 5C:
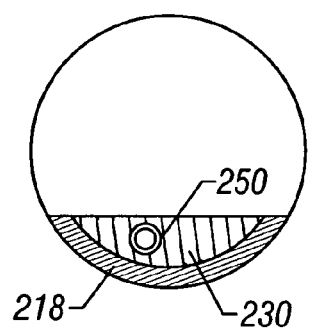

FIG. 5A illustrates a variation of the inventive device 200 having a conductive tip 204 located at the front of the transducer assembly 202. As illustrated, the conductive tip 204 may have a third conducting member (e.g., a wire) electrically coupled directly to the conductive tip 204. However, this configuration requires an elongate member 218 with a diameter larger than that of the transducer assembly 202 to accommodate a wire along side of the transducer assembly 202. It may be desirable to minimize the diameter of the transducer assembly 202 so that the device 200 may fit within the working channel of a bronchoscope or other endoscope. FIG. 5B illustrates another variation of the inventive device 200 which attempts to minimize the size of the elongate sheath 218. As illustrated in FIG. 5B, the transducer assembly 202 may have an outer perimeter that is smaller than an inner perimeter of a lumen of the elongate member 218 such that the third conducting member 250 extends along the lumen and parallel to the transducer assembly 202. As shown in FIG. 5C, which is a side view of the variation of FIG. 5B, this variation of the transducer assembly 202 has a non-circular shape to permit passage of the third conducting member 250 along the side of the transducer assembly 202. As shown, the elongate member 218 may have a retaining epoxy 230 placed within the elongate member 218 to secure the third conducting member 250 and to seal any opening in the distal end caused by the difference in size between the transducer assembly 202 and the elongate member 218.

Figure 5D:
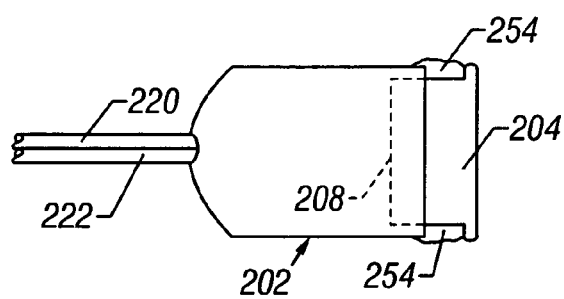

FIG. 5D illustrates another variation used to minimize the size of the device. For sake of illustration, FIG. 5D only illustrates the transducer assembly 202, conducting members 220, 222, tip 204, and transducer 208 (hidden lines.) As discussed above, the transducer assembly 202 will have a conductive medium (not shown) placed on an outside surface. FIG. 5D illustrates a second conductive medium 254 placing the tip 204 in electrical communication with the first conductive medium (not shown.) This configuration permits delivery of energy to the tip 204 via one of the conducting members 220 or 222. Therefore, the need for a separate conducting member is eliminated. It should be noted that the amount of second conductive medium 254 is shown for illustrative purposes only. Moreover, the second conductive medium 254 may be located between the tip 204 and the transducer 208. In such a case, an epoxy (not shown) may be used to secure the tip 204 to the transducer assembly 208. The second conductive medium 254 may be any conductive material (e.g., gold, silver, tantalum, copper, chrome, or any biocompatible conductive material, etc. Furthermore, the second conductive material 254 may be different or the same material as the first conductive material. In the latter case, the device will appear to have a single conductive material. In FIG. 5D, the second conductive medium 254 is shown to be a coating or deposition. However, as discussed herein, the conductive mediums are not limited as such.

When using a second conductive medium 254 to provide the energy supply to a conductive tip 204 it may be desirable to provide a conductive medium 254 of sufficient thickness so that the energy delivered to the tip 204 does not produce unwanted heating of the overall transducer assembly 202. As discussed above, conducting member(s) were sized to provide sufficient energy while minimizing heating of the member. In practice, the device used gold foils having a thickness ranging from 2-10 microns.

Figure 5E:
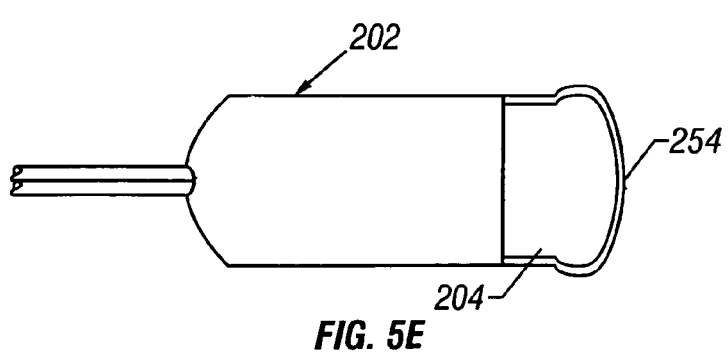

FIG. 5E illustrates a variation of the device where the tip 204 of the transducer assembly 202 is covered with the second conductive material 254. Such a configuration may be used when using a tip 204 that is not bio-compatible. For example, as discussed above, a tip 204 comprised of aluminum may offer excellent acoustic characteristics. However, an aluminum tip 204 may not offer the desired bio-compatibility. Accordingly, coating the tip 204 with the second conductive material 254 where it is exposed to tissue may provide the desired bio-compatibility characteristics. In this configuration it will be necessary to provide the second conductive material 254 in sufficient amounts such that it may deliver sufficient energy to the tip 204 while not reducing performance of the transducer assembly 202. It was found that in using an aluminum tip 204 a gold coating of 5-10 microns was sufficient to deliver sufficient energy to the tip 204. Moreover, because 10 microns corresponds to approximately ¹⁄₄₀th of a wavelength (when using 8 Mhz frequency), the thickness of the coating provided very little signal degradation.

Figure 6A:
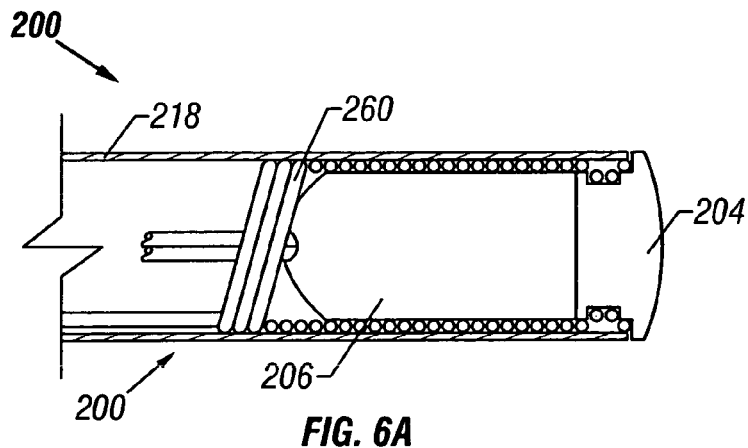
FIGS. 6A-6B show sectional views of the inventive device where a conductive medium also serves to attach a tip to the device.

FIG. 6A illustrates a variation of the inventive device where the second conductive medium is formed from a spring 260. The spring 260 may be formed from one or more spring wound wires. The wire(s) forming the spring 260 may extend through the device but ultimately couple to an energy source. In such a case, there is a need for an insulation between the spring 260 and the covering 206 or any exposed portion of any conducting members. For example, it was found that two wires of 0.005" diameter wound into a spring was of sufficient size to conduct sufficient current to the tip 204 without resulting in unwanted heating of the wires. Or, the spring 260 may be coupled to the covering 206 or one of the conducting members for delivery of the energy through the spring 260 to the tip 204. As illustrated, the spring 260 may optionally be secured (e.g., crimped, welded, soldered, glued, or reduced in diameter) about the tip 204 as additional means to retain the tip 204. Moreover, a beneficial feature of the spring 260 is that it provides additional flexibility to the end of the device when articulated in a bronchoscope.

Figure 6B:
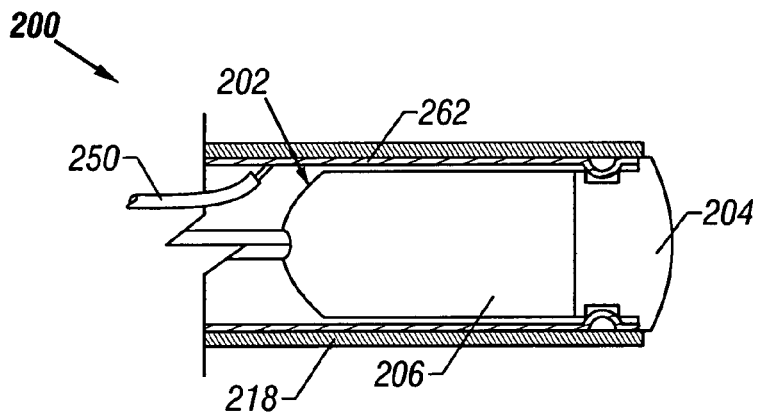

FIG. 6B illustrates another variation of the inventive device 200. In this variation, the second conductive medium comprises a tube 262. The tube 262 may be independently connected to an energy source via a third conducting member 250 (as illustrated.) In such cases, it may be necessary to insulate respective portions of the tube 262 from parts of the transducer assembly 202. Alternatively, the tube 262 may be in electrical communication with a portion of the transducer assembly 202 which supplies the energy to the tip 204. As shown, the tube 262 may optionally be secured (e.g., crimped, or reduced in diameter) about the tip 204. It is noted that the tube 262 may have a cross-sectional shape to match the outer shape of the transducer assembly 202 (e.g., circular, oval, rectangular, etc.) The tube 262 may be a hypo-tube comprised of any conductive and preferably bio-compatible material.

FIGS. 7A-7E illustrate examples of configurations for redundant joints to retain the tip 204 with the device by increasing the retention strength of the tip 204 within the device. It is contemplated that these concepts may be combined as necessary with the variations of the invention disclosed herein.

Figure 7A:
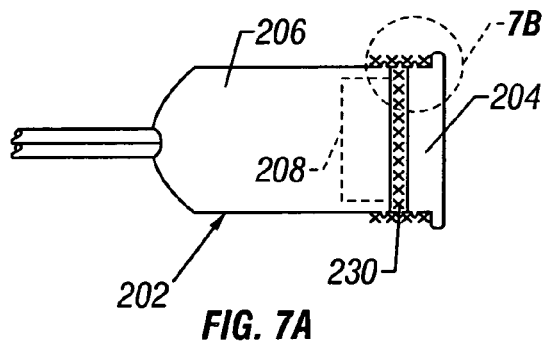
FIGS. 7A-7E illustrate various configurations to retain a tip to devices of the present invention.
Figure 7B:
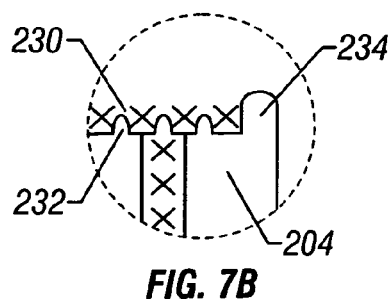

FIG. 7A illustrates a tip 204 attached to the transducer assembly 202. The tip 204 may be bonded, via a retaining epoxy 230, to either the transducer 208 or to the first conductive medium, such as a gold coating, etc. (not shown.) Naturally, the retaining epoxy 230 should be selected to minimize any interference to the source or return signal. Examples of the retaining epoxy 230 include Epotech 301, Epotech 353, Epotech 377, provided by Epoxy Technology, Inc., Bellerica, Mass. As illustrated in FIG. 7A, the retaining epoxy 230 may run along the sides of the transducer assembly 202 in which case the epoxy 230 may adhere to the elongate member (not shown.) Moreover, the tip 204 may be machined, etched, etc., to contain a plurality of small grooves 232 for seating the retaining epoxy 230. Such a configuration increases the retention strength of the tip 204 within the device and is shown in FIG. 7B which illustrates a magnified view of the section marked 7B found in FIG. 7A. Although not shown, the epoxy 230 may be placed on a lip 234 of the lens 204. In such cases, the epoxy 230 may also adhere to a front end of the elongate member (not shown.)

Figure 7C:
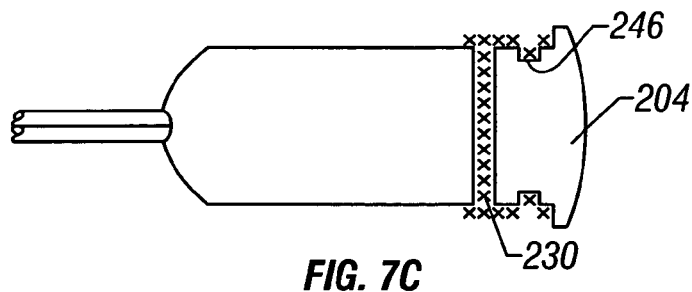

FIG. 7C illustrates another variation where the tip 204 has a single groove 246 for better retention of the tip 204 in the device. It is noted that the grooves discussed herein may either extend around the entire perimeter of the tip 204 or they may extend over only portions of the tip 204. In the latter case, the term 'groove' is intended to include structures such as: dimples, furrows, indentations, pockets, notches, recesses, voids, etc. For sake of illustration, the elongate member is not illustrated in these figures.

Figure 7D:
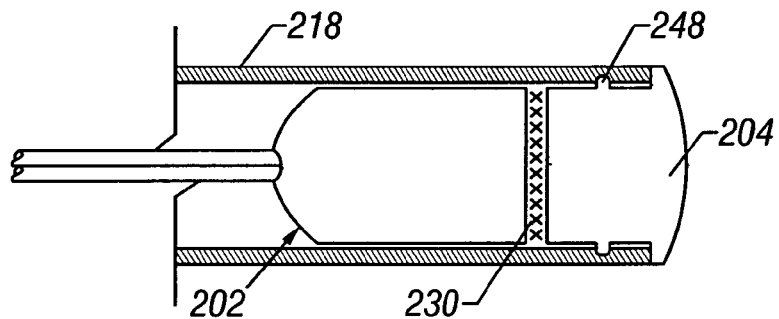

FIG. 7D illustrates a variation of a tip 204 having at least one rib 248 which may provide a friction fit with the elongate member 218. The rib 248 may be deformable or rigid.

Figure 7E:
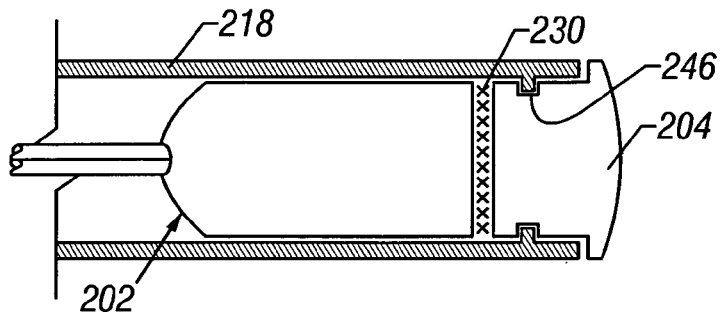

FIG. 7E illustrates another variation of the invention where the tip has a at least one grove 246 where the elongate member 218 is either crimped or filled into the groove 246. The elongate member 218 may also be reformed using heat such that it forms/flows into the groove 246.

Figure 8:
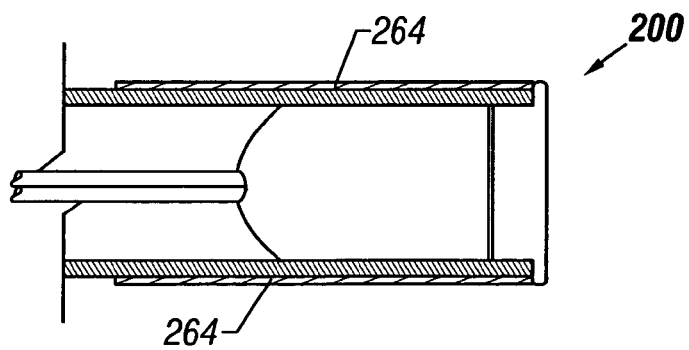
FIG. 8 illustrates an insulating layer on the device.

FIG. 8 illustrates a variation of the device 200 with an insulating layer 264 on the distal end of the device 200. The insulating layer 264 may be a coating, sleeve, etc. which prevents heat generated by the device from adversely affecting either tissue or the transducer assembly. The insulating layer 264 may extend over a limited area of the device as needed. Examples of the insulating layer 264 materials include polyimide, silicone, PTFE, FEP, PFA.

Figure 9A:
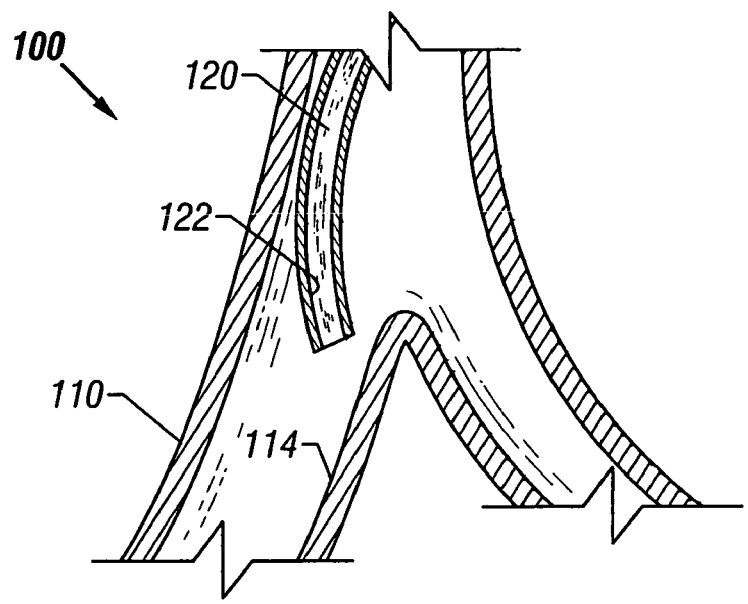
FIGS. 9A-9C shows the device when used to create a collateral channel in the airways of the lung.
Figure 9B:
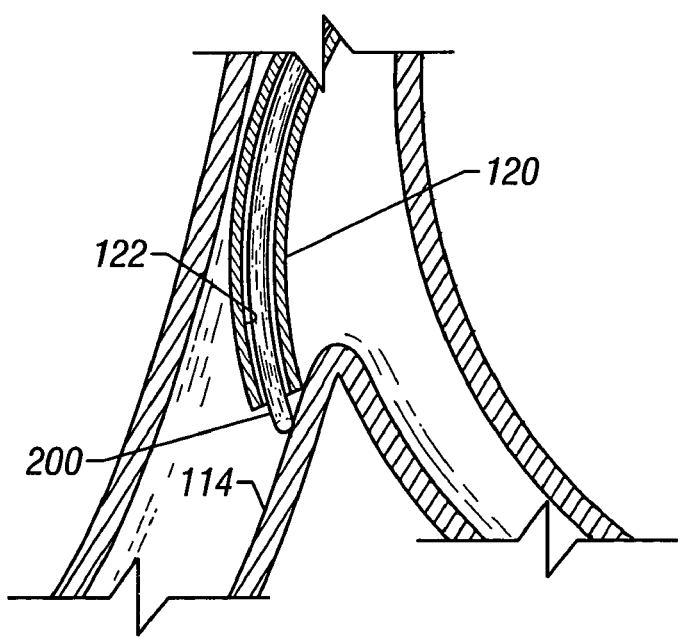
Figure 9C:
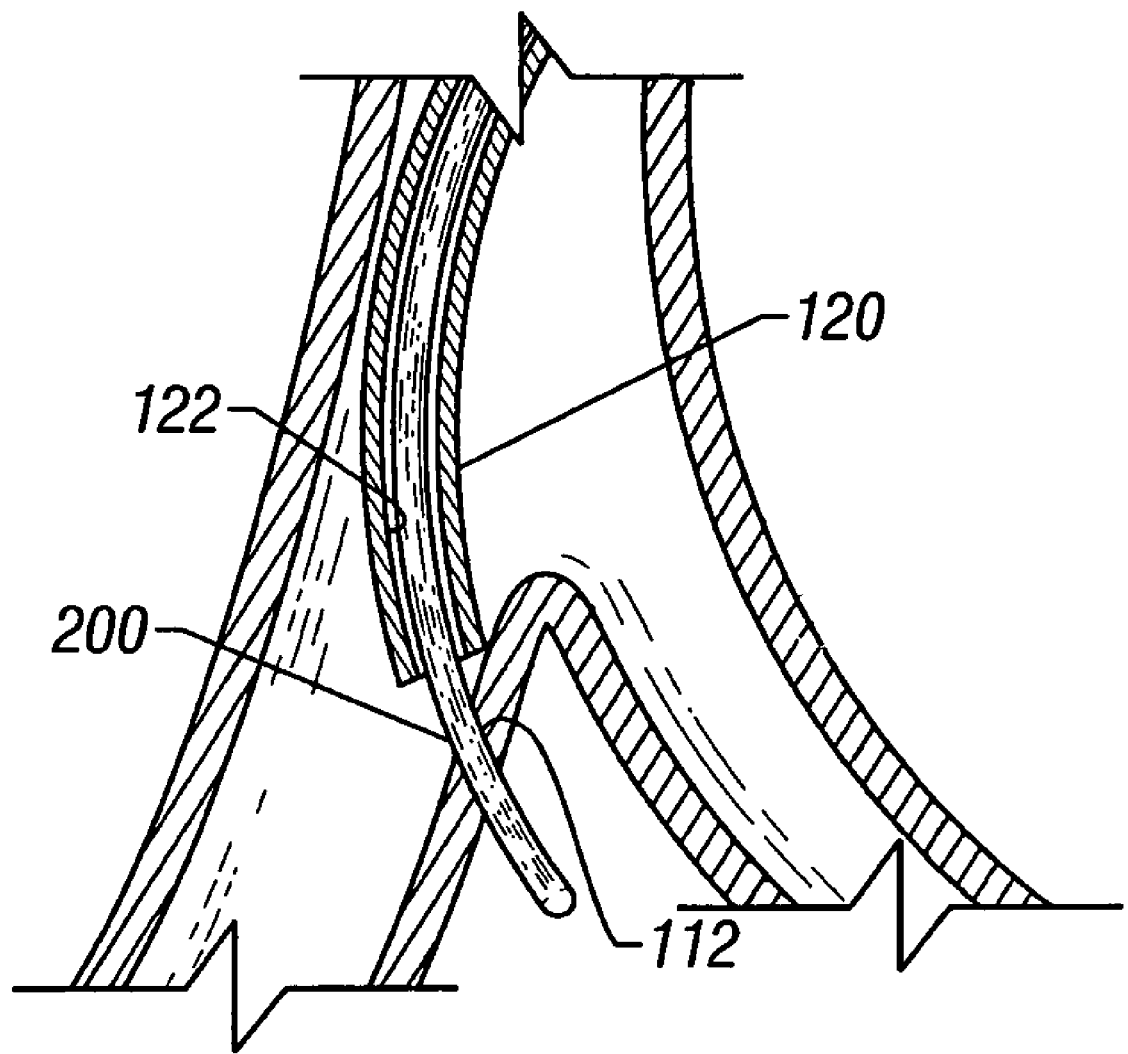

FIG. 9A-9C illustrates use of the device within a lung to create a collateral channel in the airway wall tissue. FIG. 9A illustrates the advancement of an access device 120 into the airways 100 of a lung. The access device may be a bronchoscope, endoscope, endotracheal tube with or without vision capability, or any type of delivery device. The access device 120 will have at least one lumen or working channel 122. The access device 120 will locate an approximate site 114 for creation of a collateral channel. In cases where the access device 120 is a bronchoscope or similar device, the access device 120 is equipped so that the surgeon may observe the site for creation of the collateral channel. In some cases it may be desirable for non-invasive imaging of the procedure. In such cases, the access device 120 as well as the other devices discussed herein, may be configured for detection by the particular non-invasive imaging technique such as fluoroscopy, "real-time" computed tomography scanning, or other technique being used.

FIG. 9B illustrates a variation of the inventive device 200 advanced through the channel 122 of the access device 120 towards the site 114. The site 114 is then inspected to determine whether a blood vessel is adjacent to the site.

FIG. 9C illustrates the creation of a collateral channel 112. As shown in FIG. 9C, the device 200 may be manipulated to a position that is optimal for creation of the collateral channel 112. It is noted that either the access device 120 or the inventive device 200 may be steerable. Such a feature may assist in the positioning of any of the devices used in the inventive method. Although it is not illustrated, as discussed herein, it is desirable to create the collateral channel such that it is in fluid communication with an air-sac. The fluid communication allows for the release of trapped gasses from the hyper-inflated lung.

The inventive device is configured to communicate with an analyzing device or control unit 190 adapted to recognize the reflected signal or measure the Doppler shift between the signals. As mentioned above, the source signal may be reflected by changes in density between tissue. In such a case, the reflected signal will have the same frequency as the transmitted signal. When the source signal is reflected from blood moving within a vessel, the reflected signal has a different frequency than that of the source signal. This Doppler effect permits determination of the presence or absence of a blood vessel within tissue. The device may include a user interface which allows the user to determine the presence or absence of a blood vessel at the target site. Typically, the user interface provides an audible confirmation signal. However, the confirmation signal may be manifested in a variety of ways (e.g., light, graphically via a monitor/computer, etc.)

Although depicted as being external to the device 200, it is contemplated that the analyzing device 190 may alternatively be incorporated into the device 200. The transducer assembly of the invention is intended to include any transducer assembly that allows for the observation of Doppler effect, e.g., ultrasound, light, sound etc.

In variations of the invention using pulsed Doppler, the selection of the tip length, as discussed above, sets an important parameter for design of the Doppler pulse length and range gate so that excessive echo signal clutter caused by the use of titanium is reduced before the arrival of the echo signals from the area of interest.

The transmit pulse length is set to be less than the acoustic travel time for an echo signal from the area of tissue to be inspected. This setting allows the receiver to begin recovery from the transmit pulse before the first echo signal arrives at the transducer. As shown in FIG. 10A, the gated gain control and carrier are set based upon the time-of-flight (TOF) of a signal given pre-desired depths at which the device listens for blood vessels.

The values discussed herein are intended to serve as examples only with the underlying calculations being intended to show the methodology used for Doppler detection of blood vessels. For example, during trials it was found that an acceptable minimum and maximum depth of penetration of the device was 0.8 mm and 10 mm respectively. It is noted that depths are often measured as being normal to the surface of the tissue, and because the device will often approach the tissue at an angle to the surface of the tissue, the maximum and minimum ranges $R_{max}$ and $R_{min}$ used for determining the TOF are adjusted to reflect the normal distance from the tip of the device to the desired depth. (e.g., assuming a 60 degree angle of incidence, and a minimum and maximum depths of 0.8 mm and 10 mm, $R_{min}$=0.92 mm and $R_{max}$=11.55 mm.)

The time for a signal to travel from the tip to and from $R_{min}$ equals $2R_{min}/C_{tissue}$ where $C_{tissue}$ equals the speed of the signal in tissue (approximately 1540 m/s). The time for a signal to travel back and forth through the tip (assuming a 1.33 mm titanium tip, with $C_{titanium}$=6100 m/s) was found to be 0.44 μs. Therefore, the time for the closest echoes of interest is approximately 1.2 μs plus 0.44 μs or 1.64 μs. The Transmit Pulse Length is then set to be less than time for the closest echoes of interest, preferably about ½ of 1.64 μs or ~0.82 μs. Setting the Transmit Pulse Length to be less than the time for the closest echoes of interest allows the receiver to begin recovery from the reverberation of the transmit pulse in the titanium tip before the first echo signals arrives back at the transducer. As a result, the controller is configured to listen for the first Doppler echo signal starting at the earliest time the first echo signal will return. Based upon the above example, this time is 1.64 μs.

Using a combination of a gated gain control applied to the receiver and a gated carrier applied to the demodulator, the Doppler echo signals are thereafter received until a time that echoes return from the deepest area of interest (e.g., as noted above, 10 mm). This value is calculated based upon the TOF from the tip to the deepest area of interest (15 μs, calculated from $2R_{max}/C_{tissue}$.) plus the TOF through the tip (0.44 μs as discussed above.) Accordingly, Doppler signals from tissue of up to 1 cm of depth ($R_{max}$) may be received up to 15.44 μs. FIG. 10B illustrates the above calculated values as applied to the TOF diagram. As noted above, these values are intended to be exemplary and illustrate the methodology used in determining the timing for the Doppler system. Accordingly, these values may also be adjusted depending upon the desired depth to be examined.

Figure 10C:
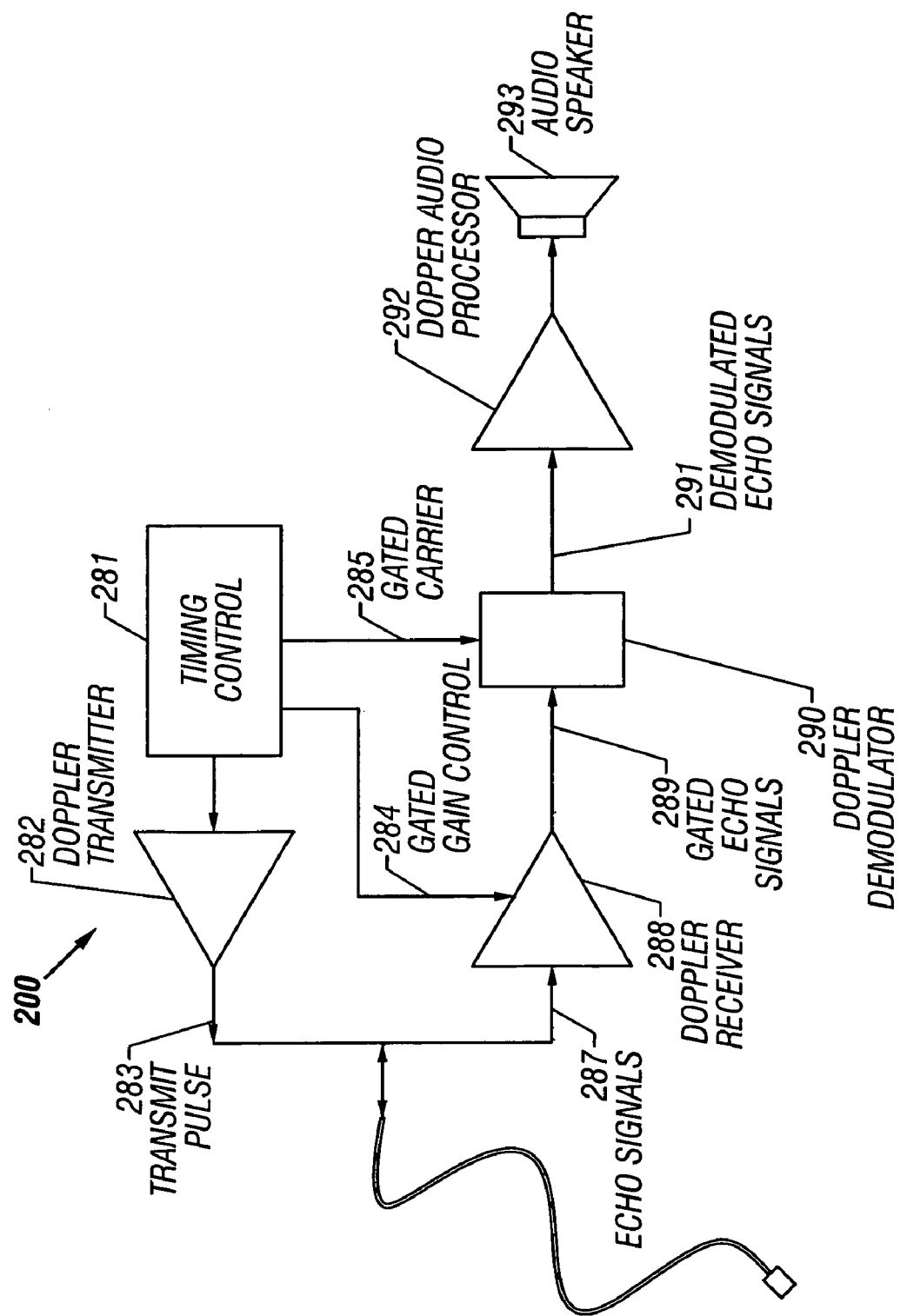
FIG. 10C illustrates an example of a schematic representation of a pulsed wave Doppler electronic system for use with the inventive device.

FIG. 10C illustrates an example of a schematic representation of a pulsed wave Doppler electronic system for use with the inventive device. The electronics system uses standard circuit elements.

As illustrated, the timing control 281 supplies timing and control signals to the Doppler transmitter 282, the Doppler receiver 288, and the Doppler demodulator 290. The Doppler transmitter 282 amplifies an applied signal applied to generate a transmit pulse which is ultimately applied to the device 200. In one example, the transmit pulse, had a center frequency of 8 MHz and a pulse length of approximately 1 μs and an amplitude of 15 V peak. The transducer at the distal tip of the device 200 converts the transmit pulse into an acoustic pulse. As the acoustic pulse travels through the tissue and blood the structures and cells produce reflections that travel back toward the probe tip and there converted from acoustic echoes to electrical echo signals 287. These echo signals 287 consist of a mixture of signals, some of a frequency equal to that of the transmitted signal (echoes from stationary structures in the ultrasonic field), and some echoes that are shifted in frequency by the Doppler effect. The echo signals 287 are amplified by the Doppler receiver 288. A gated gain control 284 is set to start increasing gain after the transmit pulse ends but soon enough for echo signals 287 of interest to be amplified. The gated gain control 284 lasts until echo signals 287 from the deepest structures of interest have been amplified. These echo signals 287 are demodulated in the Doppler demodulator 290 using a gated carrier 285 in order to produce demodulated echo signals 291 that contain Doppler signals from moving blood cells at audio frequencies. The demodulated echo signals 291 are then filtered and amplified by the Doppler audio processor 292 to improve the signal fidelity of the Doppler audio signals. These filtered and amplified signals are then sent to the Audio Speaker 293.

It is also noted that the device may also designed to have a double shield. First, the twisted pair wires connecting the transducer assembly to the Doppler control unit 190 will be shielded. Furthermore, because the energy supply 188 may be delivered through one of the pair of wires, the outer portion of the catheter that is exposed proximal to the working channel of an endoscope will also be shielded to prevent undesirable conduction of current.

We claim:

1. A medical device for applying energy to tissue, the medical device comprising:
   an elongate member having a proximal portion and a distal portion;
   a transducer assembly located entirely within an interior of the elongate member and towards said distal portion of said elongate member,
   an RF tissue-cutting electrode comprising an electrically conductive tip located entirely distally to said transducer assembly at a distal end of said distal portion of said elongate member, said tip having a front face covering said distal end of said distal portion, said tip being adapted to conduct energy to tissue, said tip having a front and back surface, said back surface being in acoustical communication with said transducer assembly wherein said tip is adapted to communicate a source signal from said transducer assembly out through said surface, said tip also being adapted to communicate a reflected signal said front surface to said transducer assembly; and at least two conducting members extending through at least a portion of said elongate member, at least one of said conducting members capable of electrically coupling an RF energy supply to said tip to electrosurgically remove tissue.

2. The medical device of claim 1, wherein a length of said tip is selected from a multiple of one-quarter of said wavelength of said signal.

3. The medical device of claim 2, wherein said length of said tip is approximately seven-quarters of said wavelength of said signal.

4. The medical device of claim 1, wherein said tip comprises a material selected from the group consisting of titanium, aluminum, and stainless steel.

5. The medical device of claim 1, wherein the tip comprises an electrically conductive coating about at least a portion of the tip.

6. The medical device of claim 1, wherein the tip is adapted as a lens to disperse the signal over a substantial portion of an outer surface of the tip.

7. The medical device of claim 1, wherein the tip is adapted to direct the signal toward the ultrasonic transducer.

8. The medical device of claim 1, wherein the tip has a substantially flat surface.

9. A catheter comprising:
a proximal section, a flexible intermediate section, a distal section, and a distal end;
a blood vessel sensor means comprising an ultrasonic transducer, said ultrasonic transducer adapted to emit and receive ultrasonic signals; and
an electrosurgical cutting means for cutting tissue comprising an electrode located entirely distally to said ultrasonic transducer and attached to said distal end of said catheter, said electrode being connected to an energy source, and said electrode and said ultrasonic transducer being positioned such that when ultrasonic signals are emitted and received by said ultrasonic transducer said signals are transmitted through said electrode.

10. The catheter of claim 9, wherein a length from the ultrasonic transducer to the distal end is selected from a multiple of one-quarter of a wavelength of said the ultrasonic signal.

11. The catheter of claim 10, wherein the length from the ultrasonic transducer to the distal end is approximately seven-quarters of the wavelength of said the ultrasonic signal.

12. The catheter of claim 9, wherein the distal section comprises a material selected from the group consisting of titanium, aluminum, and stainless steel.

13. The catheter of claim 9, wherein said catheter comprises an insulating material.

14. The catheter of claim 9, wherein the distal end comprises an electrically conductive coating about at least a portion of the distal end.

15. The catheter of claim 9, wherein the distal end is adapted as a lens to disperse the signal over a substantial portion of an outer surface of the distal end.

16. The catheter of claim 9, wherein the distal end is adapted to direct the signal toward the ultrasonic transducer.

* * * * *

UNITED STATES PATENT AND TRADEMARK OFFICE
CERTIFICATE OF CORRECTION

PATENT NO. : 7,422,563 B2
APPLICATION NO. : 10/080344
DATED : September 9, 2008
INVENTOR(S) : Roschak et al.

It is certified that error appears in the above-identified patent and that said Letters Patent is hereby corrected as shown below:

Column 5, line 28, "related" should read --relates--.

Column 7, line 22, "shows" should read --show--.

Column 11, line 66, delete "a".

Column 13,
line 65, "204" should read --240--.
line 66, "204" should read --240--.

Column 14,
line 1, "204" should read --240--.
line 10, "SB" should read --5B--.

Column 18, line 44, insert --be-- between "also" and "designed".

Column 19, line 4 Claim 1, insert --from-- between "signal" and "said front surface".

Signed and Sealed this

Sixteenth Day of December, 2008

JON W. DUDAS
*Director of the United States Patent and Trademark Office*